(12) United States Patent
Gutmann et al.

(10) Patent No.: US 8,778,696 B2
(45) Date of Patent: Jul. 15, 2014

(54) PROCESSING UNITS AND METHODS FOR THE PROCESSING OF LIQUID SAMPLES

(75) Inventors: Oliver Gutmann, Thalwil (CH); Edwin Oosterbroek, Cham (CH); Michael Glauser, Rotkreuz (CH); Michael Andreas Heinrich, Zurich (CH); Jean-Pierre Bolliger, Buchrain (CH); Emad Sarofim, Hagendorn (CH); Rainer D. Jaeggi, Thalwil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 528 days.

(21) Appl. No.: 12/850,949

(22) Filed: Aug. 5, 2010

(65) Prior Publication Data

US 2011/0189785 A1    Aug. 4, 2011

(30) Foreign Application Priority Data

Aug. 7, 2009 (EP) .................... 09167521

(51) Int. Cl.
*G01N 33/00* (2006.01)
*B01L 3/00* (2006.01)

(52) U.S. Cl.
USPC ......... 436/180; 422/503; 422/501; 435/287.1

(58) Field of Classification Search
None
See application file for complete search history.

(56) References Cited

U.S. PATENT DOCUMENTS

| | | | |
|---|---|---|---|
| 5,519,635 A | 5/1996 | Miyake et al. | |
| 5,638,986 A | 6/1997 | Tuominen et al. | |
| 6,311,713 B1 | 11/2001 | Kaartinen | |
| 6,444,172 B2 | 9/2002 | Fukunaga et al. | |
| 2002/0039783 A1 | 4/2002 | McMillan et al. | |
| 2003/0091477 A1 | 5/2003 | Paul et al. | |
| 2003/0094206 A1 | 5/2003 | Gerhardt et al. | |
| 2005/0095602 A1 | 5/2005 | West et al. | |
| 2005/0161669 A1 | 7/2005 | Jovanovich et al. | |

FOREIGN PATENT DOCUMENTS

| | | |
|---|---|---|
| JP | 2002282682 | 10/2002 |
| JP | 2006247533 | 9/2006 |
| WO | 2004/103564 A1 | 12/2004 |
| WO | 2008/039875 A1 | 4/2008 |
| WO | 2008/089767 A1 | 7/2008 |

OTHER PUBLICATIONS

Lee, Chia-Yen et al. "Integrated microfluidic systems for cell lysis, mixing/pumping and DNA amplification." Journal of Micromechanics and Microengineering (2005) 15 1215-1223.*

(Continued)

*Primary Examiner* — Christopher A Hixson
(74) *Attorney, Agent, or Firm* — Dinsmore & Shohl LLP

(57) ABSTRACT

A microfluidic processing unit for the automated processing of liquid samples and method thereof are disclosed. In one embodiment, the unit comprises first and second main channels connected to a pump for generating a negative or positive pressure therein; a sample channel which supplies a liquid sample is connectable to a sample vessel containing the liquid sample, the sample channel communicates with the first main channel and is equipped with an on/off valve; one or more reagent channels for supplying one or more reagents, the reagent channels being connectable to reagent vessels containing reagents for reacting with the liquid samples, each of the reagent channels communicating with the first or second main channel and being equipped with an on/off valve; and a reaction chamber for reacting a sample and reagent, the reaction chamber being connected to the first and second main channels via at least one on/off valve.

10 Claims, 17 Drawing Sheets

(56) References Cited

OTHER PUBLICATIONS

Wang, Ling et al. "Determination of estrogens in water by HPLC-UV using cloud point extraction." Talanta (2006) 70 47-51.*

Waters, Larry C. et al. "Multiple sample PCR amplification and electrophoretic analysis on a microchip." Analytical Chemistry (1998) 70 5172-5176.*

European Search Report, Serial No. EP09167521, Search completed Mar. 12, 2010, 7 pgs.

Japan Patent Office Official Action dated Jan. 29, 2013 in co-pending Japanese Patent Application No. 2010-176299 filed May 8, 2010.

Jorgensen, et al., A Biochemical Microdevice With an Integrated Chemiluminescence Detector, www.sciencedirect.com, Sensors and Actuators, B 90 (2003) pp. 15-21.

* cited by examiner

PROCESSING UNITS AND METHODS FOR THE PROCESSING OF LIQUID SAMPLES

TECHNICAL FIELD

The present disclosure relates to microfluidic processing units and methods for the automated processing of liquid samples.

BACKGROUND

In recent years, a strong demand for the automated analysis of liquid samples can be observed which is primarily due to the fact that there is an ongoing increase in the number of clinical analyses. Sample analysis typically is based on mixing the samples with one or more reagents for causing analyte-specific reactions, followed by detecting the reaction products to determine absence/presence or concentration of one or more analytes contained therein.

Commercially available analyzers typically make use of pipetting robots for mixing of samples and reagents. Such pipetting robots normally have many fast and nearly continuously moving parts, which may often require frequent maintenance and replacement operations. In addition, conventional analyzers have limited flexibility with regard to the type of the analytical method that can be performed and typically can only be operated with comparably low precision due to the variability of pipetting operations. Furthermore, in such conventional analyzers since reagents are typically exposed to the ambient air, the reagents used therewith may have a reduced shelf life.

Due to low sample consumption, fast analysis times and high sample throughput, many efforts have been made to develop integrated fluidic systems, among these microfluidic systems, for the automated analysis of liquid samples. However, conventional microfluidic systems have many drawbacks since they are limited to predefined workflows and fluid volumes and typically are related to a dedicated type of analytical method. They are provided with a comparably small number of reagent channels and therefore may not be up-scaled according to the demands of the user. Reagents have to be supplied by pipetting operations or via complex tubing to the reagent channels. In addition, microfluidic systems are normally intended for single-use only and therefore are often associated with having comparably large costs.

SUMMARY

In one embodiment, a microfluidic processing unit for the automated processing of liquid samples is disclosed, and comprises: at least one first main channel and at least one second main channel connected to a pump for generating a negative or positive pressure therein; at least one sample channel for supplying liquid sample connectable to a sample vessel containing the liquid sample, the sample channel communicating with the first main channel and being equipped with an on/off valve; one or more reagent channels for supplying one or more reagents, the reagent channels being connectable to reagent vessels containing reagents for reacting with the liquid samples, each of the reagent channels communicating with the first or second main channel and being equipped with an on/off valve; and at least one reaction chamber in which a reaction between a sample and reagent can takes place, the reaction chamber being connected to the first and second main channels via at least one on/off valve.

In another embodiment, a method for the automated processing of liquid samples is disclosed, and comprises: providing a processing unit according to one or more embodiments of the invention; drawing a predefined volume of reagent into the vent-sided portion of the first main channel; drawing the liquid sample into the sample channel; drawing a predefined volume of the liquid sample into the pump-sided portion of the first main channel; drawing the predefined volume of liquid sample into the at least one reaction chamber; drawing the predefined volume of the reagent into the at least one reaction chamber to generate a sample/reagent mixture; and detecting a reaction product of the sample/reagent mixture contained in the at least one reaction chamber.

In another embodiment, a microfluidic processing unit for the automated processing of liquid samples is disclosed, and comprises at least one set of first and second segments, each of which including: at least one first and one second main channel connected to a pump for generating a negative or positive pressure therein; at least one sample channel for supplying the liquid sample communicating with the first main channel and equipped with an on/off valve; one or more reagent channels for supplying reagents, the reagent channels being connectable to reagent vessels containing reagents for reacting with the liquid samples, each of the reagent channels communicating with the first or second main channel and being equipped with an on/off valve; and at least one reaction chamber for reaction of sample and reagent to take place, the reaction chamber being connected to the first and second main channels via at least one on/off valve, wherein the second main channel of the first segment is being connected to the sample channel of the second segment.

In still another embodiment, a method for the automated processing of liquid samples is disclosed, and comprises: providing a processing unit according to one or more embodiments of the invention; drawing a predefined volume of first reagent into the vent-sided portion of the first main channel of the first segment; drawing a predefined volume of the liquid sample into the sample channel of the first segment; drawing a predefined volume of the liquid sample into the vent-sided portion of the first main channel of the first segment; drawing the predefined volume of reagent into at least one reaction chamber of the first segment; drawing the predefined volume of the liquid sample into the reaction chamber to generate a sample/reagent mixture; drawing the sample/reagent mixture from the reaction chamber of the first segment to at least one reaction chamber of the second segment; drawing a predefined volume of second reagent into the vent-sided portion of the first main channel of the second segment; drawing the predefined volume of second reagent into the reaction chamber containing the sample/reagent mixture; and detecting a reaction product of the sample/reagent mixture contained in the reaction chamber.

These and further features and advantages of the various embodiments will appear more fully from the following description.

BRIEF DESCRIPTION OF THE DRAWINGS

The accompanying drawings, which are incorporated in and constitute a part of the specification, illustrate various embodiments of the invention, and together with the general description given above and the detailed description given below, serve to explain the principles of the invention.

DETAILED DESCRIPTION

Figure 1:
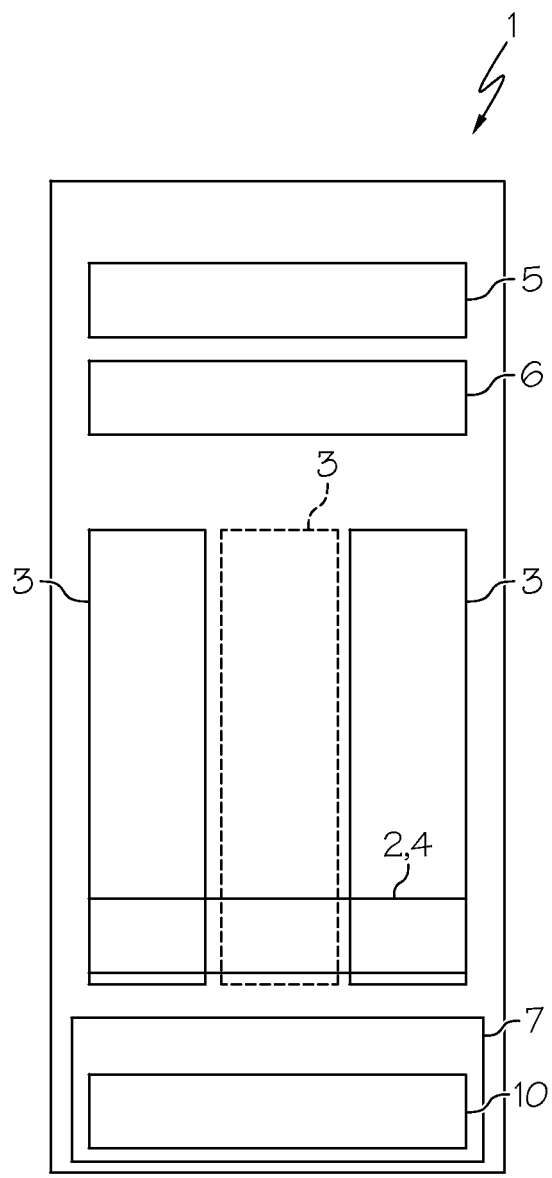
FIG. 1 depicts a schematic diagram illustrating functional entities of an exemplary configuration of a system according to one or more embodiments of the invention.

As provided hereafter, in one or more embodiments, a new microfluidic processing unit for the automated processing of liquid samples is disclosed. In the microfluidic processing unit, liquid samples can be mixed with one or more reagents with a view of an analysis thereof using a reaction product of the sample/reagent mixtures obtained.

The processing unit can be configured in various ways in accordance with specific demands of the user. In that, the processing unit according to one or more embodiments may be embodied, e.g., as a preparative instrument for preparing sample/reagent mixtures which can be transferred to an analytical instrument for analyzing a reaction product of the sample/reagent mixtures. Otherwise, the processing unit according to one or more embodiments may be coupled to an analytical unit for analyzing the samples based on the reaction product of the sample/reagent mixture obtained. The microfluidic processing unit according to one or more embodiments may be used in (bio-) chemistry including in-vitro diagnostics and can be adapted to carry out various assays comprising mixing of samples and reagents as well as detecting the result of those reactions. It may be used, e.g., for diagnostic assays such as clinical chemistry assays and immunoassays.

As used herein, the term "microfluidic processing unit" refers to a processing unit which is provided with a plurality of interconnected channels and chambers through which fluid can be transported to effect preparative and/or analytical manipulations of the samples in accordance with the specific demands of the user. The cross-sectional dimension of the microfluidic features of the processing unit typically is on the order of millimetre to sub-millimetre-scale. The microfluidic features enable manipulation of fluid volumes which, e.g., are on the order of about 100 µl or less at a flow rate which, e.g., is on the order of about 100 µl/sec or slower.

As used herein, the term "on/off-valve" denotes a valve which can be selectively brought into one of three distinct states, i.e., a first open state in which liquid and gaseous fluid can pass through the valve, a second open state in which gaseous fluid can pass through the valve and liquid fluid cannot pass through the valve, and a closed state in which both liquid and gaseous fluids are blocked to pass the valve. Such on/off-valve may be embodied as freeze-thaw valve which is well-known to those of skill in the art and in patent literature, e.g., is described in US patent application publication No. 2003/0094206 A1 and U.S. Pat. No. 6,311,713 B1.

By use of freeze-thaw valves, fluid flow can be controlled by merely freezing and thawing liquid fluid contained in a flow channel. Stated more particularly, in the first valve open state, liquid and gaseous fluid can pass through the valve. In the second valve open state, while gaseous fluid can pass through the valve, the valve is sufficiently cooled to generate a frozen plug in case of presence of liquid fluid so that the second valve open state can be changed into the valve closed state. In the valve closed state, freeze-thaw valves rely on the resistance to shearing motion that is obtained between the resulting frozen plug and the channel wall thereby to restrict fluid flow. In combination with on/off valves such as freeze-thaw valves, flow channels can be used for transiently keeping (i.e. registering) and providing a fluid in a predefined place without having a gas bubble in-between the valve and the fluid.

As used herein, the term "fluidically connected" or "connected" refers to communicating lines, channels or other system components which may include fluid flow regulating means such as on/off valves, external actuators, including mechanical actuators and the like. Accordingly, fluidically connected system components may be open to allow for fluid flow or may be closed to block fluid flow.

Liquid samples for processing by a processing unit according to one or more embodiments of the invention are fluids in which one or more analytes can potentially be found. Samples can be chemical and the processing unit can be adapted to carry out one or more chemical assays, e.g., drug interaction screening, environmental analysis, identification of organic substances and the like. Samples can also be biological and may include blood, serum, urine, cerebrospinal fluids and nucleic acids containing fluids and any other fluid of interest as long as processing thereof involves mixing of the fluid with one or more reagents.

As used herein, the term "reagent" is used to indicate any liquid, which can be mixed with sample and/or one or more other reagents. In the more strict sense of the term, reagents include components which can react with the sample. Reagents, however, can also be non-reacting fluids such as buffers and diluting fluids.

According to one embodiment, the microfluidic processing unit for the automated processing of liquid samples contains gaseous and optionally liquid system fluid. It may particularly contain a combination of gaseous and liquid system fluid. The system fluid is used for transporting fluids such as samples and reagents by generating positive or negative (atmospheric) pressures within the channels and/or chambers, wherein mixing between liquid system fluid and samples or reagents is avoided.

In one embodiment, the microfluidic processing unit comprises at least two main channels—at least a first main channel and a second main channel—both of which are connected to a pump, in the following denoted as "main pump", for generating negative or positive (atmospheric) pressures therein. The first main channel may be provided with a vent for introducing gaseous system fluid into the processing unit. Also, the second main channel may be provided with a vent for introducing gaseous system fluid into the processing unit. Pumps of the microfluidic processing unit may, e.g., be embodied as continuous pumps or discontinuous pumps such as pumps of the membrane pump type, syringe pump type, rotary displacement pump type and bellow pump type. Pumps of the bellow pump type, e.g., are disclosed in U.S. Pat. No. 5,638,986.

The processing unit may further comprise at least one sample channel for supplying liquid sample which is connectable to a sample vessel containing the sample. In one embodiment, the sample vessel is not included in the processing unit. In another embodiment, the sample vessel is included in the processing unit and the sample channel is connected to the sample vessel. The sample may, e.g., be drawn from the sample vessel into the sample channel by means of a sample intake such as a suction tube. The sample channel is communicating with the first main channel and is being equipped with an on/off valve so as to enable or block sample flow from the sample channel to the first main channel by use of the on/off-valve.

The processing unit may further comprise one or more reagent channels for supplying one or more reagents which are connectable to reagent vessels containing reagents for reacting with the liquid samples. In one embodiment, the one or more reagent vessels are not included in the processing unit. In another embodiment, the one or more reagent vessels are included in the processing unit and the one or more reagent channels are fluidically connected to the one or more reagent vessels. Reagents contained in the reagent vessels may be equal or different with respect to each other. Each of the reagent channels communicates with the first main channel or second main channel and is being equipped with an on/off valve so that, by use of the on/off-valves, reagent flow from the reagent channels to the first or second main channel can be enabled or blocked. It may, e.g., be preferred to locate each of the on/off valves of the reagent channels adjacent to an opening where the reagent channels open into the first or second main channel.

The processing unit may yet further comprise one or more reaction chambers for reaction of liquid sample and one or more reagents to take place. The at least one reaction chamber is fluidically connected to the first and second main channels via at least one on/off valve, e.g., by means of a first reaction chamber port connecting the reaction chamber to the first main channel and a second reaction chamber port connecting the reaction chamber to the second main channel. Each of the reaction chamber ports may be equipped with an on/off valve so as to enable or block fluid flow between the reaction chamber and the first and second main channels, respectively. The at least one reaction chamber may particularly be interconnected between the first and second main channels. In case of plural reaction chambers, the reaction chambers are in parallel arrangement with respect to each other. In order to enable reaction between sample and one or more reagents, the at least one reaction chamber may, e.g., be embodied as incubating chamber adapted for incubating the sample/reagent mixture contained. While incubating sample/reagent mixtures, the mixtures are kept at one or more predefined temperatures during one or more predefined time intervals.

In one embodiment of the processing unit, it may be preferred that the first main channel is equipped with an on/off valve located in-between a vent and the main pump so as to partition the first main channel into a vent-sided portion and a pump-sided portion. In that case, the one or more reagent channels communicate with the vent-sided portion of the first main channel while the sample channel communicates with the pump-sided portion of the first main channel. Accordingly, a predefined volume of reagent can be provided in the first main channel adjacent to the on/off valve of the first main channel. Otherwise, by use of the on/off valve of the first main channel, pump generated negative or positive pressure can be enabled or inhibited to act on the vent-sided portion of the first main channel.

In the above described embodiment of the processing unit, it may be preferable that an opening where the sample channel opens into the first main channel is located adjacent to the on/off valve of the first main channel with the on/off-valve of the sample channel being arranged adjacent to the on/off valve of the first main channel. In that case, sample contained in the sample channel adjacent to the on/off-valve of the sample channel can be drawn into the pump-sided portion of the first main channel without having gas bubbles in-between the on/off valve of the first main channel and the sample.

In the above described embodiment of the processing unit, it may yet be preferable that the processing unit comprises one or more first reagent channels (i.e. a first set of reagent channels) for supplying one or more reagents which can be connected to first reagent vessels, each of which containing reagent for reacting with the liquid samples. In one embodiment, the one or more first reagent vessels are not included in the processing unit. In another embodiment, the one or more first reagent vessels are included in the processing unit and the one or more first reagent channels are connected to the one or more first reagent vessels. The reagents contained in the first reagent vessels may be equal or can be different with respect to each other. Each of the first reagent channels communicates with the vent-sided portion of the first main channel and is being equipped with an on/off valve so as to enable or block reagent flow from the first reagent channels to the first main channel by use of the on/off-valves. Each of the on/off valves may in particular be located adjacent to an opening where the first reagent channels open into the first main channel.

In the above case, the processing unit may further comprise one or more second reagent channels (i.e. a second set of reagent channels) different from the first reagent channels for supplying one or more reagents which can be connected to second reagent vessels different from the first reagent vessels, each of which containing reagent for reacting with the liquid samples. In one embodiment, the one or more second reagent vessels are not included in the processing unit. In another embodiment, the one or more second reagent vessels are included in the processing unit and the one or more second reagent channels are being connected to the one or more second reagent vessels. The reagents contained in the second reagent vessels may be identical or can be different with respect to each other. The reagents contained in the second reagent vessels may be equal to or different from reagents contained in the first reagent vessels. Each of the second reagent channels communicates with the second main channel and is equipped with an on/off valve so as to enable or block reagent flow from the second reagent channels to the second main channel by use of the on/off-valves. Each of the on/off valves may in particular be located adjacent to an opening where the second reagent channels open into the second main channel.

In case of providing for one or more second reagent channels, the second main channel may preferably be equipped with one or more on/off valves in correspondence to the number of reaction chambers, wherein each of the on/off valves is associated to one of the reaction chambers. Furthermore, each of the on/off valves is being arranged in-between an opening where the associated reaction chamber opens into the second main channel and the pump. It may be preferred that each of the on/off valves is located adjacent to the opening of the second reaction chamber port wherein the on/off valve via which the reaction chamber is being connected to the second main channel is being located adjacent to the on/off valve of the second main channel so that reagent can be drawn into the second reaction chamber port without having gas bubbles in-between reagent and the on/off valve of the second reaction chamber port.

According to yet another embodiment, the processing unit may comprises preferably another pump, which in the following is denoted as "auxiliary pump." The auxiliary pump is different from the main pump and is connected to the sample channel for generating negative or positive (atmospheric) pressures therein. Providing for the auxiliary pump, manipulation of sample within the sample channel can be decoupled from manipulation of sample and/or reagent in the main channels and reaction chambers, respectively, so that the main and auxiliary pumps can be used in parallel in order to interleave fluid manipulation steps in order to save time in processing the liquid samples.

According to yet another embodiment, which in particular may be combined with the above described embodiment that includes an auxiliary pump, it may be preferable that the sample channel is connected to one or more mixing chambers via at least one on/off valve, e.g., by means of first and second mixing chamber ports. Each of the mixing chambers is being provided with mixing means adapted for mixing the sample by performing a reciprocating movement of the sample which, e.g., may be generated by the auxiliary pump. The mixing chamber ports may be equipped with the on/off valve so as to enable or block sample flow between the mixing chamber and the sample channel. In case of plural mixing chambers, the mixing chambers may, e.g., be arranged in parallel arrangement with respect to each other.

According to yet another embodiment, which in particular may be combined with above described embodiment that includes an auxiliary pump, it may be preferable that the processing unit further comprises at least one diluting fluid channel for supplying diluting fluid, e.g. water, for diluting the samples. The diluting fluid channel can be connected to a diluting fluid vessel containing fluid adapted for diluting the samples. The diluting fluid channel communicates with the sample channel and is being equipped with an on/off valve which preferably is located adjacent to an opening where the diluting fluid channels opens into the sample channel.

In the above described embodiment of the processing unit, it may be preferable that the sample channel be equipped with an on/off valve arranged in-between an opening where the diluting fluid channel opens into the sample channel and the sample vessel with the on/off valve being located adjacent to the on/off valve of the diluting fluid channel so that diluting fluid can be transferred to the sample channel without gas bubbles in-between the diluting fluid and the on/off valve of the sample channel.

According to yet another embodiment, it may be preferable that the at least one reaction chamber be equipped with mixing means adapted for mixing fluid by performing a reciprocating fluid movement caused by positive or negative pressures generated by the main pump. In that case, each of the reaction chambers can advantageously be used for mixing fluid to prepare sample/reagent mixtures.

According to yet another embodiment, it may be preferable that the processing unit be coupled to an analytical unit including at least one detector for detecting a reaction product of the sample/reagent mixture contained in the at least one reaction chamber, wherein the analytical unit is adapted for analyzing the sample based on the detected reaction product. In case of plural reaction chambers it may particularly be preferred to provide for one detector adapted for detecting reaction products of sample/reagent mixtures contained in the plural reaction chambers.

According to yet another embodiment, the processing unit may further comprise a main washing unit including a fluid container containing washing fluid connected to the first and second main channels for supplying washing fluid to the main channels and one or more reaction chambers. According to yet another embodiment, the processing unit may further comprise an auxiliary washing unit including a fluid container containing washing fluid connected to the sample channel for supplying washing fluid to the sample channel and, as the case may be, one or more mixing chambers.

As also described herein after, in one or more embodiments, a new method for the automated processing of liquid samples is disclosed. The method is implemented by the above-described processing unit of the invention. Accordingly, the method includes providing a processing unit for the automated processing of liquid samples as-above described which may be embodied according to any one or any combination of the above-described embodiments.

In one embodiment, the method may include drawing a predefined volume of reagent into the vent-sided portion of the first main channel. It may include drawing the sample into the sample channel to be kept in a predefined position identified as register position. It may include drawing a predefined volume of the sample into the pump-sided portion of the first main channel. It may include drawing the predefined volume of sample into at least one reaction chamber. It may include drawing the predefined volume of reagent into at least one reaction chamber. It may include detecting a reaction product of the sample/reagent mixture contained in the reaction chamber.

According to an embodiment of the method, the predefined volume of reagent and the predefined volume of sample preferable are simultaneously drawn into the at least one reaction chamber. Alternatively, sample and reagent may be separately drawn into the reaction chamber. In that, first sample may be drawn into the reaction chamber, followed by drawing reagent into the reaction chamber, and vice versa.

According to further embodiments of the method, the method includes one or more of the following:

mixing sample and reagent within the at least one reaction chamber;

mixing sample and reagent within the pump-sided portion of the first main channel;

mixing sample within the at least mixing chamber connected to the sample channel; and washing channels and/or chambers using washing fluid.

In still other embodiments, another new microfluidic processing unit for the automated processing of liquid samples is disclosed. The processing unit comprises at least one set of first and second segments. Each of the first and second segments includes:

at least two main channels, i.e. at least one first main channel and one second main channel, connected to a pump for generating negative or positive pressures therein, wherein the first main channel and/or the second main channel may be provided with a vent for introducing gaseous system fluid;

at least one sample channel for supplying the liquid sample which communicates with the first main channel and is equipped with an on/off valve;

one or more reagent channels for supplying reagents which are connectable to reagent vessels containing reagents for reacting with the liquid samples, wherein each of the reagent vessels is communicating with the first main channel or the second main channel and is equipped with an on/off valve; and at least one reaction chamber for reaction of sample and reagent to take place, wherein the reaction chamber is fluidically connected to the first and second main channels, e.g., through first and second reaction chamber ports, respectively, via at least one on/off valve; each of the reaction chamber ports may be equipped with the on/off valve; the at least one reaction chamber may particularly be interconnected between the first and second main channels.

In the above described processing unit, in one embodiment the first and second segments are serially arranged with respect to each other. In that, the second main channel of the first segment is fluidically connected to the sample channel of the second segment so that sample/reagent mixture contained in the at least one reaction chamber of the first segment can be transferred to the reaction chamber of the second segment, e.g., for mixing with another reagent.

According to an embodiment, the processing unit comprises a third segment which comprises a sample channel including a first sample channel portion and a second sample channel portion. Both the first and second channel portion are being connected to a pump for generating positive or negative pressures therein. The third segment further includes one or more mixing and registering chambers fluidically connected to the first and second sample channel portions, e.g., through first and second mixing chamber ports, via at least one on/off valve. The one or more mixing and registering chambers may in particularly be fluidically interconnected between the first and second sample channel portions. Each of the mixing chamber ports may be provided with the on/off valve. In the third segment of the processing unit of the invention, the first sample channel portion is fluidically connected to a sample vessel containing the sample. Furthermore, the second sample channel portion of the third segment is fluidically connected to the sample channel of the first segment. In that case it may be preferred that the sample channel is connected to a diluting fluid channel for supplying diluting fluid adapted for diluting the sample. Accordingly, sample can be transferred from the sample vessel to the sample channel of the third segment, can be mixed by the mixing and registering chambers and/or can be diluted by the diluting fluid channel, and can then be transferred to the sample channel of the first segment. Due to the separate pump, in-taking, mixing and diluting of the sample can be performed independently of the second and third segments of the processing unit.

According to another embodiment, the first main channel is equipped with an on/off valve in-between the vent and the pump, wherein one or more reagent channels communicate with a vent-sided portion of the first main channel and wherein the sample channel communicates with a pump-sided portion of the first main channel.

According to another embodiment of the invention, the processing unit is coupled to an analytical unit including one detector for detecting a reaction product contained in the reaction chambers of the first and second segments. Accordingly, the detector is a shared component shared by the segments and the reaction chambers.

According to another embodiment, another new method for the automated processing of liquid samples is disclosed. The method comprises one or more of:

providing a processing unit as above-described in connection with the third aspect of the invention;

drawing a predefined volume of first reagent into the vent-sided portion of the first main channel of the first segment;

drawing a predefined volume of sample into the sample channel of the first segment;

drawing a predefined volume of sample into the vent-sided portion of the first main channel of the first segment;

drawing the predefined volume of reagent into at least one reaction chamber of the first segment;

drawing the predefined volume of sample into the reaction chamber to generate a sample/reagent mixture;

drawing the sample/reagent mixture from the reaction chamber of the first segment to at least one reaction chamber of the second segment;

drawing a predefined volume of second reagent into the vent-sided portion of the first main channel of the second segment;

drawing the predefined volume of second reagent into the reaction chamber containing the sample/reagent mixture; and detecting a reaction product of the sample/reagent mixture contained in the reaction chamber.

In the processing unit according to one or more embodiments, some on/off valves are indicated to be located adjacent to each other which means that they are located exactly at an intersection (i.e. corner) of communicating fluid channels. Hence, fluids can be provided in one fluid channel without having a gap in-between so that, e.g., sample and reagent may be attached to each other. Adjacent on/off valves, however, are just a preferred option. Alternatively, on/off valves of communicating fluid channels may also be separated from the intersection of the fluid channels. In the latter case, a gaseous or liquid system fluid filled gap may be present in-between fluids provided in one fluid channel.

The above-described embodiments of the invention may be used alone or in any combination thereof without departing from the scope of the invention.

By way of illustration, specific exemplary embodiments in which the various embodiments may be practiced are described hereafter with reference now made to the drawings.

Figure 2:
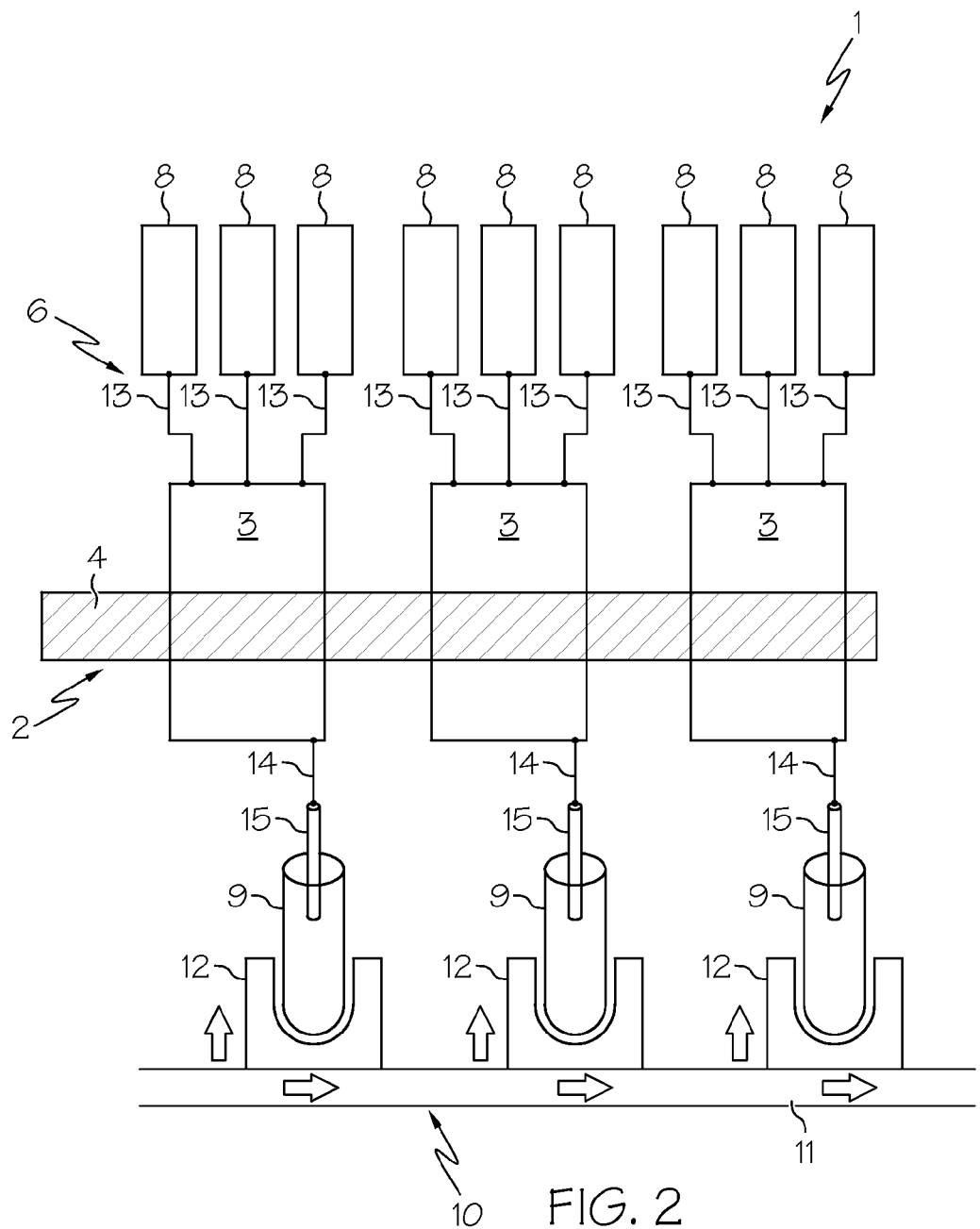
FIG. 2 depicts a schematic diagram depicting an exemplary embodiment of the configuration of FIG. 1.
Figure 3:
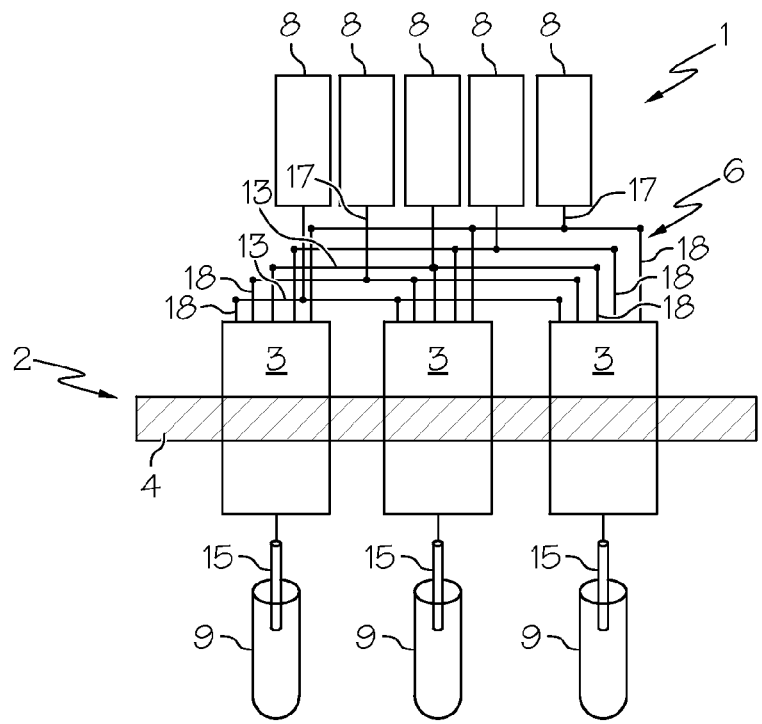
FIG. 3 depicts a schematic diagram depicting another exemplary embodiment of the configuration of FIG. 1.

Referring to FIGS. 1 to 3 an exemplary first configuration of the system according to one or more embodiments of the invention for analyzing liquid samples and exemplary embodiments thereof are explained.

Accordingly, the system 1 for the processing of liquid samples includes a plurality of (flow-through) processing units 3 adapted for processing of liquid samples, each of which being a functional and structural entity of the system 1. It further comprises an analytical unit 2, which includes one optical detector 4 which, e.g., may be embodied as photometer. The processing units 3, together with the analytical unit 2 including the optical detector 4, are dedicated to a same type of analytical method which, e.g., can be related to clinical chemistry, immune chemistry, nucleic acid testing, haematology, urinalysis and the like according to the specific demands of the user. The system 1 further comprises a reagent unit 5 provided with a plurality of reagent vessels or containers 8, e.g., stored in a cooled compartment which contain reagents for mixing with the samples. The reagents may be identical or different with respect to each other. The system 1 yet further comprises a sample unit 7 equipped with a sample tube loading mechanism 10 for loading sample tubes 9 into the system 1 and transporting the sample tubes 9 to the various processing units 3. The system 1 yet further comprises a distribution unit 6 for distributing one or more reagents provided with plural distribution (flow) channels for transporting reagents and optionally samples to each of the processing units 3.

With particular reference to FIG. 2, an exemplary embodiment of the first configuration of the system 1 of FIG. 1 is explained. The system 1 comprises a plurality of processing units 3, each of which being connected to plural reagent containers 8 by plural distribution channels 13 provided by the distribution unit 6. While a number of three processing units 3 and a number of nine reagent containers 8 are shown for the purpose of illustration only, it is to be understood that any other number of processing units 3 and reagent containers 8, respectively, may be envisaged according to the specific demands of the user.

In the system 1, each processing unit 3 is connected to a dedicated subset of reagent containers 8 of the reagent unit 5, wherein each reagent container 8 of one subset is connected to one processing unit 3 by one distribution channel 13 so as to provide a one-to-one connection between each of the reagent containers 8 and associated processing unit 3. Accordingly, each of the distribution channels 13 fluidically connects one reagent container 8 and one processing unit 3.

In the system 1, each of the processing units 3 is further connected to one sample intake 15 by means of one sample line 14 so that samples contained in the sample tubes 9 can be aspirated into the processing units 3. The sample intakes 15 may, e.g. be embodied as metallic needles. Accordingly, each processing unit 3 can aspirate sample from a dedicated sample tube 9 by use of the sample intake 15. The sample intakes 15 may be part of the sample unit 7. The sample tube loading mechanism 10 for transferring the sample tubes 9 to the processing units 3, e.g., is embodied as belt drive including a motor-driven belt 11 provided with cup-like holders 12 for holding the sample tubes 9. Accordingly, the sample tubes 9 can be transported via the sample tube loading mechanism 10 to the processing units 3 by driving the belt 11 as indicated by the horizontal arrows. Additionally, each holder 12 can be lifted upwards so that the sample tube 9 contained therein is moved towards one sample intake 15 so as to enable aspiration of the sample contained in the sample tube 9 by the sample intake 15 as indicated by the vertical arrows.

The system 1 further includes one optical detector 4, e.g., embodied as photometer for optically detecting reaction products of sample/reagent mixtures contained in each of the processing units 3. The optical detector 4 is part of an analytical unit 2 for analyzing the samples based on the optically detected reaction products. Accordingly, the optical detector 4 is adapted to detect light emitted from reagent products of sample/reagent mixtures contained in the processing units 3. In that, the processing units 3, together with the analytical unit 2 including the optical detector 4, are dedicated to a predefined type of analytical method.

In the exemplary embodiment of the system 1 of FIG. 2, any desired number of processing units 3 can be run in parallel, while each processing unit 3 has access to an individual subset of reagents (i.e. reagent containers 8) of the reagent unit 5. Each processing unit 3 has further access to an individual sample. Hence, sample throughput can be increased according to the specific demands of the user. Otherwise, since the processing units 3 are related to a same type of analytical method, analysis of the samples even in case of failure of one or more processing units 3 can be ensured. Furthermore, by means of plural processing units 3 which are related to a same type of analytical method, parallel analysis of samples can be carried out so as to obtain plural redundant results which can be further processed, e.g., by calculating an average thereof.

The sample tube loading mechanism 10 and the optical detector 4 are common system components shared by all processing units 3. Due to the shared system components, costs of fabricating the system 1 can be remarkably reduced.

With particular reference to FIG. 3, another exemplary embodiment of the first configuration of the system 1 of FIG. 1 is explained. In order to avoid unnecessary repetitions, only differences with respect to the embodiment of FIG. 2 are explained and otherwise reference is made to explanations made in connection with FIG. 2.

In the system 1 of FIG. 3, each of the processing units 3 has access not only to a subset of reagents but also to all reagents (i.e. reagent containers 8) of the reagent unit 5. For that purpose, the distribution channels 13 of the fluid distribution unit 6 are embodied as intermediate channels, the number of which corresponds to the number of reagent containers 8 of the reagent unit 5. In order to connect the intermediate channels 13 to the processing units 3, the system 1 further includes first reagent supply lines or channels 18 which fluidically connect the processing units 3 and the distribution channels 13, wherein different first reagent supply channels 18 are connected to different distribution channels 13. The number of the first reagent supply channels 18 corresponds to the number of distribution channels 13 multiplied by the number of processing units 3 so as to have a one-to-many connection between each of the distribution channels 13 and the processing units 3. The system 1 yet further includes second reagent supply lines or channels 17 which fluidically connect the reagent containers 8 and the distribution channels 13, wherein different second reagent supply channels 17 are connected to different distribution channels 13. The number of the second reagent supply channels 17 corresponds to the number of the distribution channels 13 so as to have a one-to-one connection between second reagent supply channels 17 and distribution channels 13.

Hence, in the system 1 of FIG. 3, each processing unit 3 is connected by the first reagent supply channels 18 to each of the intermediate channels 16. Otherwise, each reagent container 8 is connected by the second reagent supply channels 17 to a dedicated intermediate channel 16 so as to connect each reagent container 8 to each of the processing units 3.

In the exemplary second embodiment of the system 1 of FIG. 3, any desired number of processing units 3 can be run in parallel with each processing unit 3 having access to all reagents (i.e. reagent containers 8) of the reagent unit 5. Hence, sample throughput can be increased as desired and all reagents can be supplied to all processing units 3. As a result, costs can be saved compared to the case of providing individual subsets of reagents for each of the processing units 3.

Figure 4:
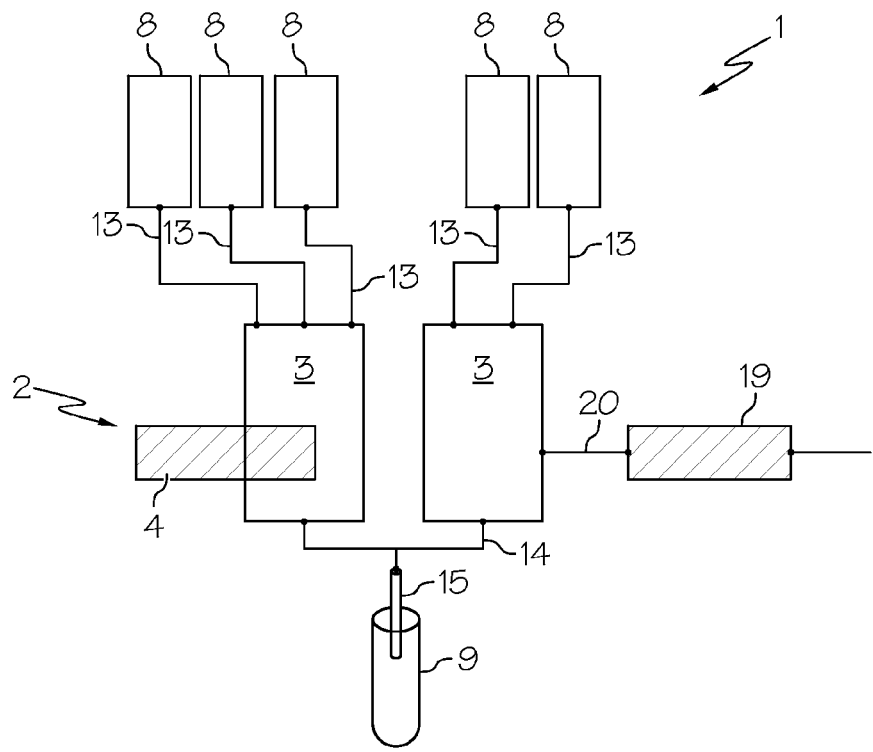
FIG. 4 depicts a schematic diagram depicting an exemplary embodiment of a variant of the configuration of FIG. 1.

With particular reference to FIG. 4, an exemplary embodiment of a second configuration of the system 1 which is a variant of the first configuration of FIG. 1 is explained. In order to avoid unnecessary repetitions, only differences with respect to the embodiment of FIG. 2 are explained and otherwise reference is made to explanations made in connection with FIG. 2.

In the second configuration of FIG. 4, the system 1 includes an analytical unit 2 which is provided with two different detectors, that is to say, an optical detector 4 and an instrument coupled flow-through cell 19. The system 1 further includes two processing units 3, wherein one processing unit 3 is coupled to the optical detector 4, e.g., embodied as photometer to detect light emitted from one or more reaction chambers and the other processing unit 3 is fluidically connected to the flow-through cell 19 by means of connecting channel 20. Accordingly, sample/reagent mixtures of the corresponding processing unit 3 can be supplied to the flow-through cell 19 for detecting reaction products of the sample/reagent mixtures by means of the instrument (not illustrated) coupled to the flow-through cell 19. The flow-through cell 19 may be coupled, e.g., to an ion-selective electrode (ISE), a biosensor such as an enzymatic-electrochemical detector, an electro-chemoluminescence detector (ECL), an optical detector or the like. Accordingly, the processing units 3, together with the optical detector 4 and the flow-through cell 19, are related to first and second types of analytical methods which are different with respect to each other. In the system 1 of FIG. 4, sample contained in one sample tube 9 can be aspirated into both processing units 3 by means of one sample intake 15 which is connected to both processing units 3 by manifold sample line 14.

In the system 1 of FIG. 4, each processing unit 3 is fluidically connected to an individual subset of reagent containers 8 which is specific to the type of analytical method used. As illustrated in FIG. 4, e.g., a number of three reagent containers 8 are used in combination with the first type of analytical method of the optical detector 4 and a number of two reagent containers 8 is used for the second type of analytical method of the flow-through cell 19. Each reagent container 8 is connected to the associated processing unit 3 by one distribution channel 13 of the fluid distribution unit 6 so as to realize a one-to-one connection between reagent containers 8 and processing units 3.

While a number of two processing units 3 related to different types of analytical methods are shown for the purpose of illustration only, it is to be understood that any other number of processing units 3, which may be related to individual types of analytical methods and which may be coupled to individual detectors may be envisaged according to the specific demands of the user.

In the exemplary embodiment of the system 1 of FIG. 4, any desired number of processing units 3 can be run in parallel, while each processing unit 3 has access to an individual subset of reagents of the reagent unit 5 which is specific to the type of analytical method used. By using one sample intake 15 connected to each of the processing units 3, one sample can be analyzed in parallel using two or more different predefined types of analytical methods.

Figure 5:
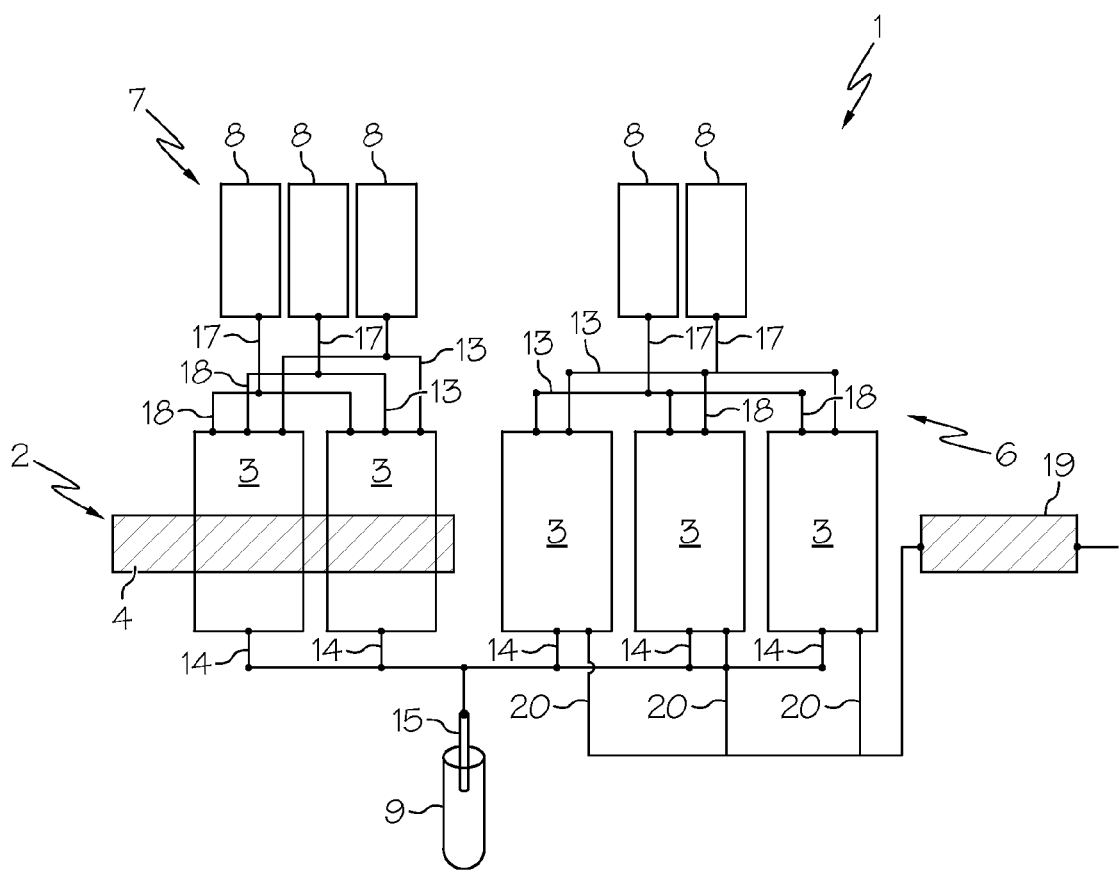
FIG. 5 depicts a schematic diagram depicting an exemplary embodiment of another variant of the configuration of FIG. 1.

With particular reference to FIG. 5, an exemplary embodiment of a third configuration of the system 1, which is another variant of the first configuration of FIG. 1, is explained. In order to avoid unnecessary repetitions, only differences with respect to the embodiment of FIG. 4 are explained and otherwise reference is made to explanations made in connection with FIG. 4.

In the embodiment of FIG. 5, the system 1 includes a first subset of (e.g. two) processing units 3 coupled to the optical detector 4 and thus related to the first type of analytical method and a second subset of (e.g. three) processing units 3 connected to the instrument coupled flow-through cell 19 and thus related to the second type of analytical method being different from the first type. The optical detector 4, e.g., may be embodied as photometer to detect light emitted from the reaction chambers of the first subset of processing units 3 coupled thereto. The flow-through cell 19 is fluidically connected to the second subset of processing units 3 by means of manifold connecting channel 20 so that sample/reagent mixtures of the reaction chambers of the second subset of processing units 3 can be transported to the flow-through cell 19 for detection thereof.

Sample of one sample tube 9 can be simultaneously aspirated into all processing units 3 of the first and second subsets by means of one sample intake 15 which is connected to all processing units 3 by manifold sample line 14. The processing units 3 of the first subset of processing units 3 which are related to the first type of analytical method have access to a first subset of reagent containers 8 of the reagent unit 5 which include all reagents (i.e. reagent containers 8) that are specific for the first type of analytical method. Otherwise, the processing units 3 of the second subset of processing units 3 which are related to the second type of analytical method have access to a second subset of reagent containers 8 of the reagent unit 5 which include all reagents (i.e. reagent containers 8) which are specific for the second type of analytical method. For that purpose, the distribution channels 13 of the fluid distribution unit 6 are comprised of a first subset of distribution channels and a second subset of distribution channels, each of which being embodied as intermediate channels. In order to fluidically connect the processing units 3 of the first subset and second subset, respectively, of processing units 3 to the first subset and second subset, respectively, of distribution channels 13, the system 1 further includes a first subset and a second subset, respectively, of first reagent supply channels 18, each of which fluidically connecting one processing unit 3 and one distribution channel 13, wherein different first reagent supply channels 18 are connected to different distribution channels 13. In order to fluidically connect the reagent containers 8 of the first subset and second subset, respectively, of reagent containers 8 to the first subset and second subset, respectively, of distribution channels 13, the system 1 yet further includes a first subset and a second subset, respectively, of second reagent supply channels 17, each of which fluidically connecting one reagent container 8 and one distribution channel 13, wherein different second reagent supply channels 17 are connected to different distribution channels 13.

In FIG. 5, while the first subset of processing units 3 includes a number of two processing units 3 coupled to the optical detector 4 and while the second subset of processing units 3 includes a number of three processing units 3 connected to the flow-through cell 19, it is to be understood that any other number of processing units 3 coupled to the optical detector 4 and flow-through cell 19, respectively, may be envisaged according to the specific demands of the user.

In the exemplary embodiment of the system 1 illustrated in FIG. 5, any desired number of processing units 3 dedicated to a specific type of analytical method can be run in parallel, while each processing unit 3 of that specific type of analytical method has access to all reagents of the reagent unit 5 specific thereto. Using one sample intake 15 connected to the processing units 3, one sample can be analyzed in parallel using different types of analytical methods, wherein each type of analytical method being related to plural processing units 3. The system 1 of FIG. 5 thus allows for a very fast analysis of samples using different types of analytical methods so as to reduce turn-around time of sample analysis. Even in case of failure of individual processing units 3, redundant fluid processing units 3 enable parallel analysis of the sample without restriction of the available analytical methods. It especially allows for determining a predefined set of parameters of one sample using different types of analytical methods in parallel.

Figure 6:
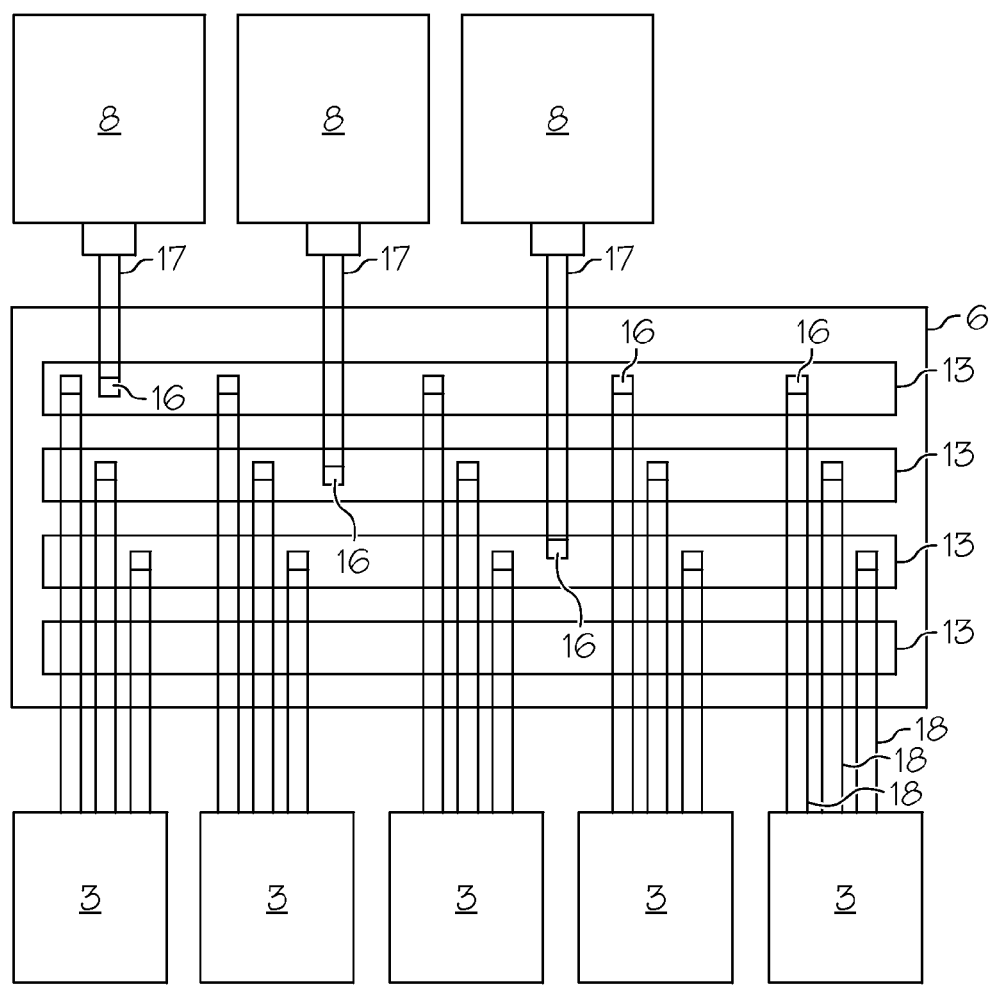
FIG. 6 depicts a schematic top view of an exemplary embodiment of the distribution unit of a system according to one or more embodiments of the invention.

Referring to FIG. 6, an exemplary embodiment of the distribution unit 6 of the system 1 as illustrated in FIGS. 3 and 5 is explained.

Accordingly, the distribution unit 6 is a solid substrate, e.g., embodied as planar board provided with plural distribution channels 13 which are in parallel alignment with respect to each other. The distribution channels 13 may be embodied as grooves worked in a surface of the substrate, e.g., covered by a foil or alternatively formed within the substrate.

Each of the processing units 3 (e.g. five processing units 3 are shown for the purpose of illustration only) has access to each of the distribution channels 13 by the first reagent supply channel channels 18. Each first reagent supply channel 18 fluidically connects one processing unit 3 and one distribution channel 13 (one-to-one connection), wherein different first reagent supply channels 18 are connected to different distribution channels 13. Each of the reagent containers 8 (e.g. three reagent containers 8 are shown for the purpose of illustration only) has access to an individual distribution channel 13 by the second reagent supply channels 17. Each second reagent supply channel 17 fluidically connects one reagent container 8 and one distribution channel 13 (one-to-one connection), wherein different second reagent supply channels 17 are connected to different distribution channels 13. The first reagent supply channels 18 are fluidically connected to the distribution channels 13 by fluidic interconnects, such as intermediate channels 16, which enable fluid to pass freely therethrough. Similarly, the second reagent supply channels 17 are fluidically connected to the distribution channels 13 by fluidic interconnects, such as intermediate channels 16, which enable fluid to pass freely therethrough. The first reagent supply channels 18 and the distribution channels 13 are arranged in different levels (vertical heights). While not shown in the figures, the first and/or second reagent supply channels 17, 18 may alternatively be part of the distribution unit 6.

In the exemplary embodiment of the distribution unit 6 of the system 1 as illustrated in FIG. 6, the distribution unit 6 is a solid substrate provided with the distribution channels 13. In a variant thereof, the solid distribution unit 6 is further provided with the first reagent supply channels 18 and/or the second reagent supply channels 17. In that case, the processing units 3 and/or the reagent containers 8 can be fluidically connected to the first and/or second reagent supply lines, e.g., by plugging the processing units 3 and/or the reagent containers 8 to dedicated ports of the distribution unit 6.

Figure 7:
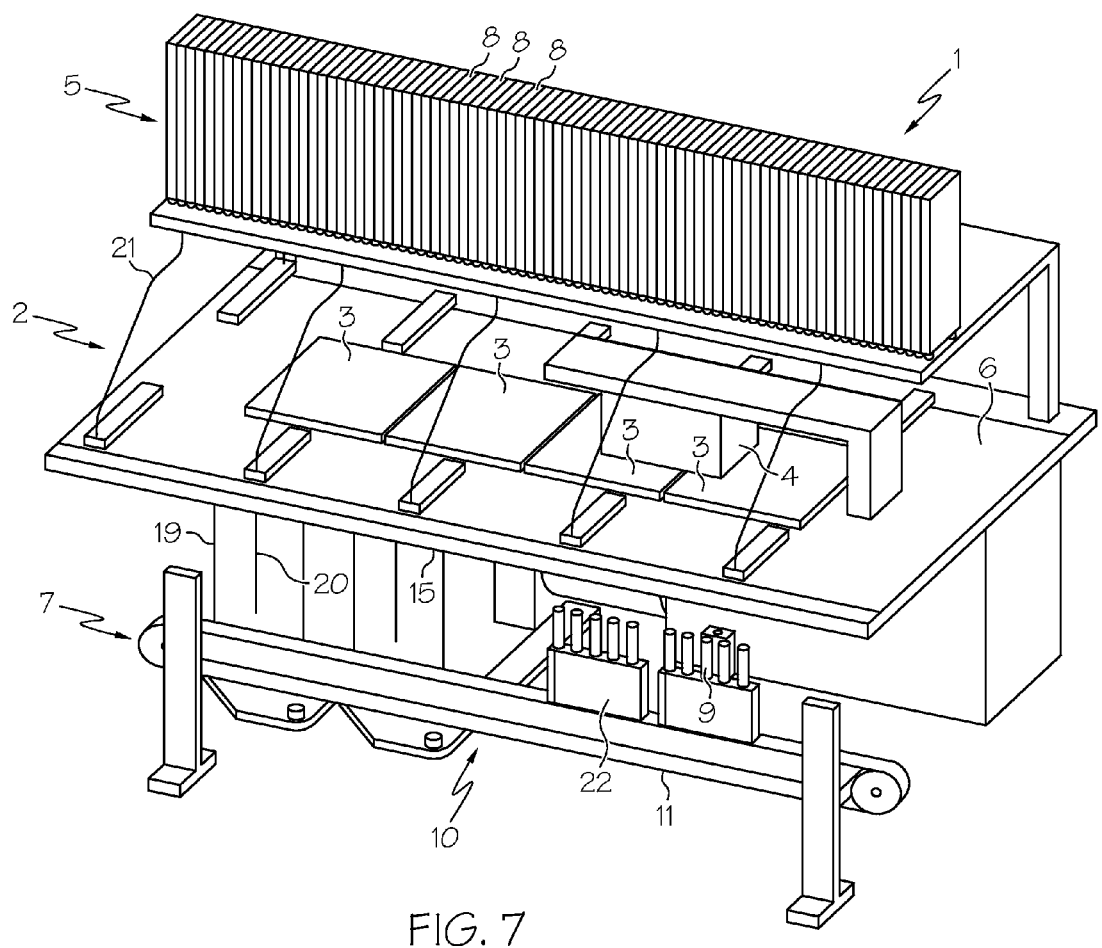
FIG. 7 depicts a perspective view of an exemplary embodiment of a system according to one or more embodiments of the invention.

Reference is made to FIG. 7 which is a perspective view of another exemplary embodiment of the system 1 according to one or more embodiments of the invention.

Accordingly, in the system 1, the sample unit 7 is provided with a sample tube loading mechanism 10 for loading sample tubes 9 into the system 1 and transporting the sample tubes 9 to each of the various processing units 3. The sample tube loading mechanism 10 is embodied as belt drive including a motor-driven belt 11 adapted for transporting a plurality of sample tube racks 22 holding the sample tubes 9.

In the system 1, the reagent unit 5 is provided with a plurality of reagent containers 8. The system 1 further includes plural processing units 3 for the processing of the samples which have a planar shape.

An analytical unit 2 includes one optical detector 4 embodied as photometer to detect light emitted from reaction products of sample and one or more reagents. The analytical unit 2 further includes one flow-through cell 19 coupled to an instrument to detect light emitted from reaction products of sample and one or more reagents transferred to the flow-through cell 19. The optical detector 4 is coupled to a first subset of processing units 3 while the flow-through cell 19 is fluidically connected to a second subset of processing units 3 by manifold connecting channel 20. The optical detector 4 and the flow-through cell 19 are related to different types of analytical methods.

In the system 1, the distribution unit 6 is a planar body which has a plate-like shape. It is provided with a plurality of distribution channels (not shown) for transporting fluids. The distribution channels are connected to the reagent containers 8 by means of second reagent supply channels 17 so as to connect each of the reagent containers 8 to a respective one of the distribution channels. Each of the processing units 3 is fluidically connected to an individual sample intake 15, e.g., embodied as a metallic needle. Each of the sample intakes 15 can be dipped into the sample tubes 9, e.g., by lifting the sample tubes 9 for aspirating sample contained therein.

As illustrated in FIG. 7, the reagent unit 5, the analytical unit 2 and the sample unit 7 are arranged in different vertical heights (levels), with the reagent unit 5 being above the analytical unit 2 and the sample unit 7 being below the analytical unit 2. Accordingly, in the system 1, reagent containers 8 can be readily replaced. Each of the units of the system 1 is a functional and structural entity and, e.g., is embodied as a modular unit.

Figure 8A:
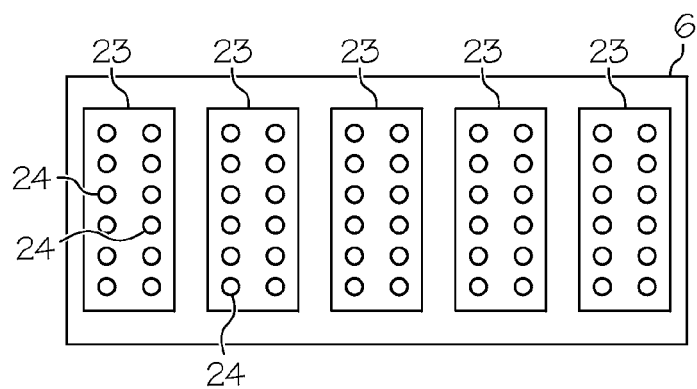
FIGS. 8A-8B depict a schematic top view (FIG. 8A) and a schematic cross-sectional view (FIG. 8B) of a distribution unit of FIG. 7.

As illustrated in FIG. 8A, which is a schematic top view of an exemplary embodiment of the distribution unit 6 of the system 1 of FIG. 7, the distribution unit 6 is provided with, e.g., five plug positions 23 (e.g. sockets), each of which being adapted for receiving one processing unit 3. Each plug position 23 is provided with plural outlet ports 24 of the distribution channels 13 which are embodied as (e.g. female) plug-in ports. Accordingly, fluid can be readily transferred between distribution channels and processing units 3 via the outlet ports 24.

Figure 8B:
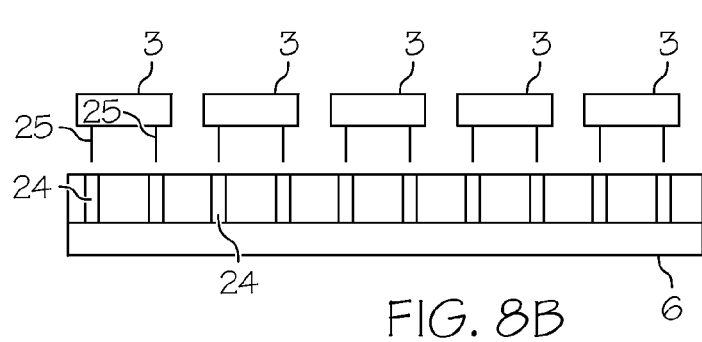

As illustrated in FIG. 8B, which is a schematic cross-sectional view of the distribution unit 6 of FIG. 8A, each of the processing units 3 is provided with plural (e.g. male) connectors 25 which can be connected (e.g. plugged-in) to the outlet ports 24 for positioning of the processing unit 3 and fluidically connecting the processing unit 3 with plural distribution channels. As each processing unit 3 has a planar shape, each one can be placed on an upper surface of the planar distribution unit 6 in parallel alignment therewith.

Figure 9A:
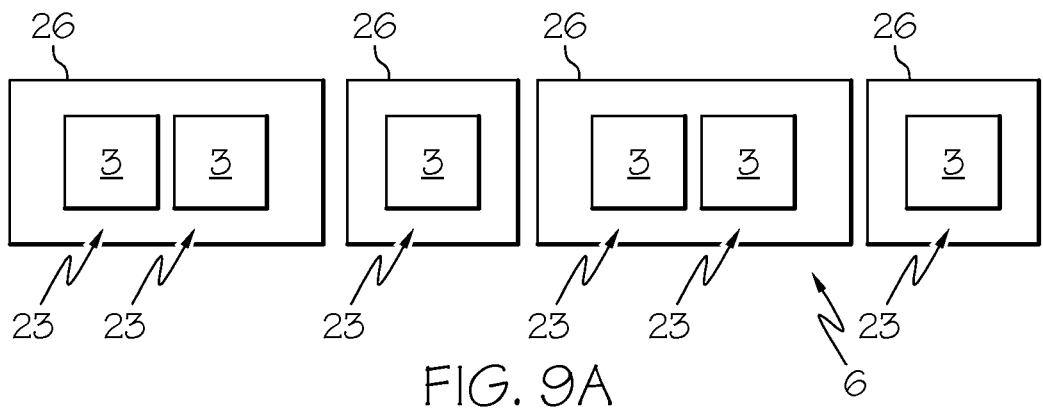
FIGS. 9A-9B depict schematic diagrams illustrating different embodiments of a distribution unit of FIG. 7.

In FIG. 9A, another embodiment of the distribution unit 6 of the system 1 of FIG. 7 is illustrated. Accordingly, the distribution unit 6 is provided with plural modular sub-units 26, each of which being provided with one or more plug positions 23 for receiving an individual subset of processing units 3. Each of the processing units 3 associated with an individual sub-unit 26 may be related, e.g., to one predefined type of analytical method. Alternatively, the processing units 3 of one subset may be related to different types of analytical methods. In the embodiment shown, the processing units 3 and/or the sub-units 26 can be easily replaced.

Figure 9B:
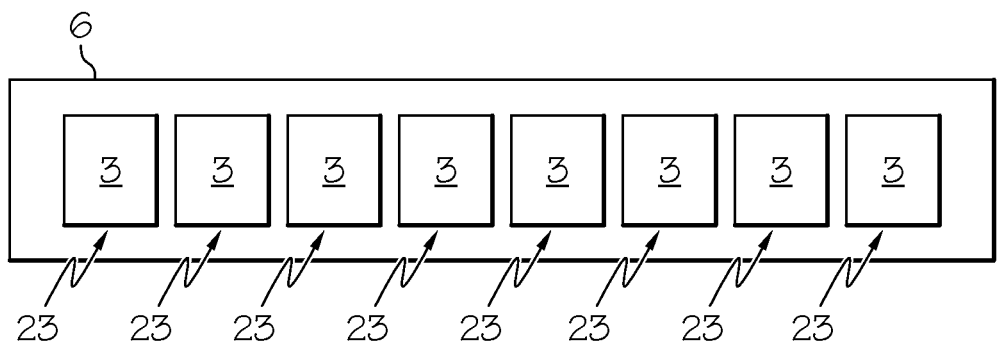

In FIG. 9B, another embodiment of the distribution unit 6 of FIG. 7 is illustrated. Accordingly, the distribution unit 6 is an integrated modular unit provided with plural plug positions 23 for receiving the processing units 3. The processing units 3 may be related to one predefined type of analytical method. Alternatively, the processing units 3 may be related to different predefined types of analytical methods.

Figure 10:
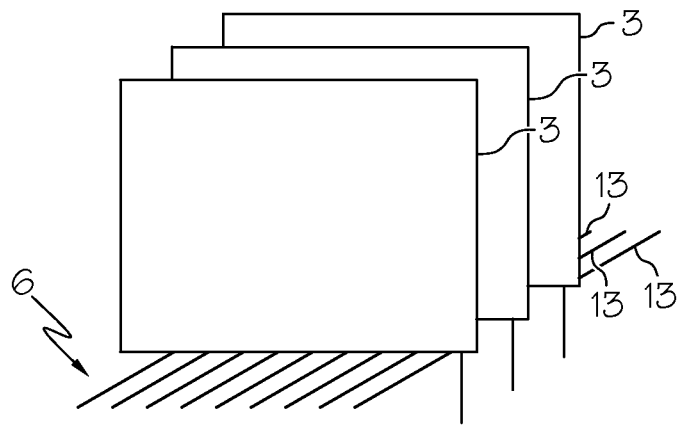
FIG. 10 depicts a schematic perspective view illustrating another embodiment of a distribution unit of FIG. 7.

Reference is made to FIG. 10 illustrating a schematic perspective view of another embodiment of the distribution unit 6 of FIG. 7. In order to avoid unnecessary repetitions, only differences with respect to the embodiment of FIGS. 8A, 8B are explained and otherwise reference is made to explanations made in connection therewith.

Accordingly, the planar distribution unit 6 is provided with plural distribution channels 13 which are in parallel alignment with respect to each other. The processing units 3 which respectively have a planar shape are in orthogonal alignment with respect to the planar distribution unit 6 having a small pitch in-between them. Such embodiment allows for a very compact arrangement of the processing units 3, which, e.g. may be plugged into plug positions 23 of the distribution unit 6. Moreover, each processing unit 3 has a small footprint for plugging with the distribution unit 6. In that case, the processing units 3 may be fluidically connected, e.g., to one or more flow-through cells 19 for detecting reaction products of samples and reagents.

Figure 11:
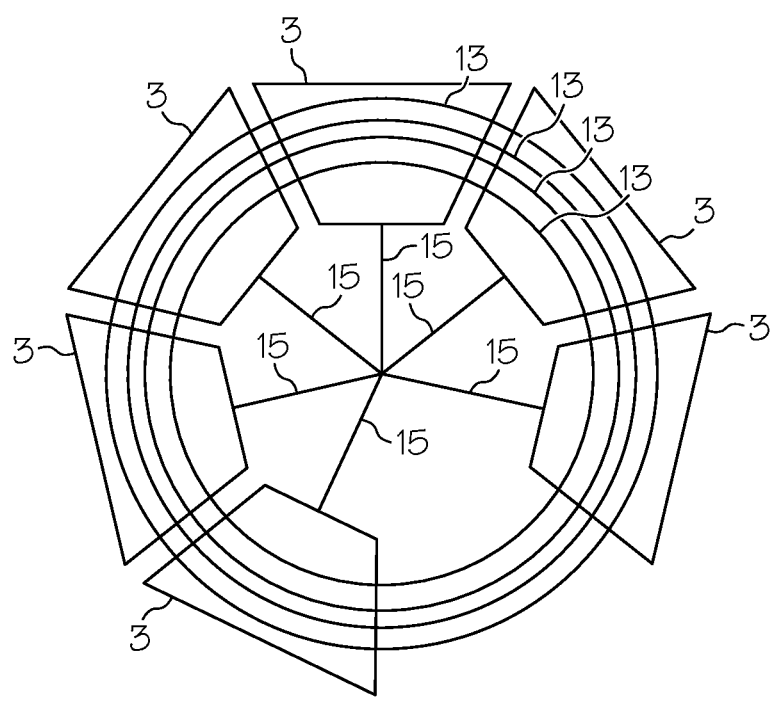
FIG. 11 depicts a schematic perspective view illustrating a yet another embodiment of a distribution unit of FIG. 7.

Reference is made to FIG. 11 illustrating a schematic top view of another embodiment of the distribution unit 6 of FIG. 7. In order to avoid unnecessary repetitions, only differences with respect to the embodiment of FIGS. 8A, 8B are explained and otherwise reference is made to explanations made in connection therewith.

Accordingly, the planar distribution unit 6 is provided with plural distribution channels 13 embodied as closed loops which are in concentric arrangement with respect to each other. The processing units 3 which have a planar shape are in parallel alignment with respect to the planar distribution unit 6 and circumferentially arranged along the closed-loop distribution channels 13. Such embodiment allows for a very compact arrangement of the processing units 3, e.g., plugged into plug positions 23 of the distribution unit 6. Each processing unit 3 is fluidically connected to a central sample intake 15 for supplying sample to the processing units 3 in parallel. The processing units 3 may be coupled, e.g., to an optical detector 4 such as a rotating photometer for optically detecting reaction products of individual samples and one or more reagents.

Figure 12:
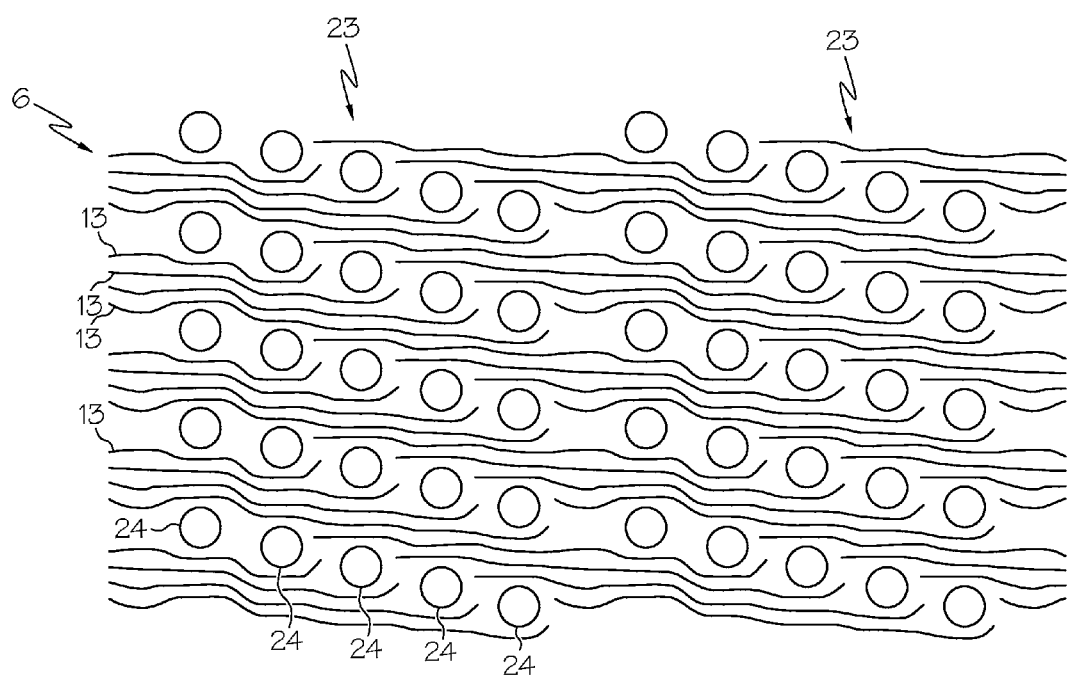
FIG. 12 depicts a schematic perspective view illustrating a yet another embodiment of a distribution unit of FIG. 7.

Reference is made to FIG. 12 illustrating a schematic top view of another embodiment of the distribution unit 6 of FIG. 7. In order to avoid unnecessary repetitions, only differences with respect to the embodiment of FIGS. 8A, 8B are explained and otherwise reference is made to explanations made in connection therewith.

Accordingly, the planar distribution unit 6 is provided with, e.g., two plug positions 23 (sockets), each of which being adapted for receiving a processing unit 3. Each plug position 23 is provided with plural outlet ports 24 of the distribution channels 13 which are embodied as (e.g. female) plug-in ports. The distribution channels 13 of the distribution unit 6 extend within first and second levels (vertical heights) different with respect to each other and can change from the first level to the second level and vice versa.

Stated more particularly, as indicated in FIG. 12, the distribution channels 13 can change from an upper first level (thicker line) to a lower second level (thinner line) or from the lower second level to the upper first level and may also branch off to neighboring distribution channels 13. Each outlet port 24 is fluidically connected to a distribution channel 13 located in the lower second level. The processing units 3 can be embodied, e.g., as "slot-cards" to be plugged into the outlet ports 24. Such an embodiment advantageously allows for a highly dense arrangement of distribution channels 13 combined with a comparably large inter-distance between outlet ports 24, such as for sealing and the like.

Figure 13:
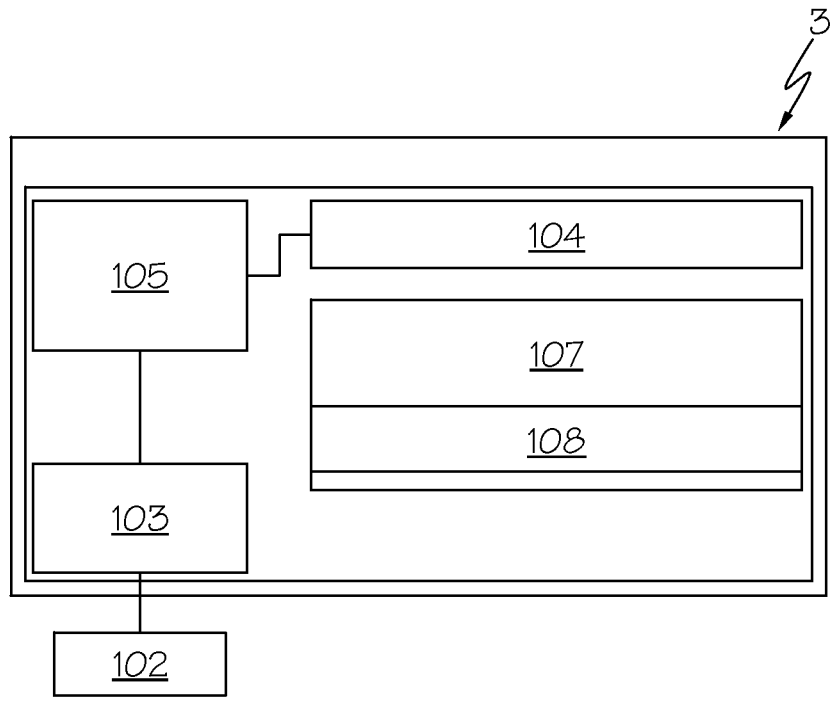
FIG. 13 depicts a schematic diagram illustrating functional entities of a first exemplary configuration of a processing unit of a system according to one or more embodiments of the invention.

Reference is made to FIG. 13 illustrating a schematic diagram of functional entities of a first exemplary configuration of the microfluidic processing unit 3 of the system 1 according to one or more embodiments of the invention used for analyzing liquid samples.

Accordingly, a processing unit 3 for the processing of liquid samples contained in sample vessel 102 includes various functional entities which include a functional entity denoted as "sample aspiration 103" connectable to the sample vessel 102 which enables liquid sample contained in the sample vessel 102 to be drawn into the processing unit 3. The functional entity sample aspiration 103 is connected to another functional entity denoted as "sample register/dilution 105" used for diluting the sample with diluting fluid and registering the sample. The functional entity sample register/dilution 105 is connected to another functional entity denoted as "sample and reagent R1/2/3 dosing 104" used for dosing sample and one or more reagents of first to third sets of reagents R1, R2 and R3. The functional entity sample and reagent R1/2/3 dosing 104 is connected to another functional entity denoted as "mixing and incubation 107" used for mixing the sample with reagent and incubating the sample/reagent mixture obtained for reaction to take place. Another functional entity denoted as "analytical unit 108" which includes a detector for detecting a reaction product of the sample/reagent mixture obtained is used for analyzing the sample based on the detected reaction product.

Figure 14:
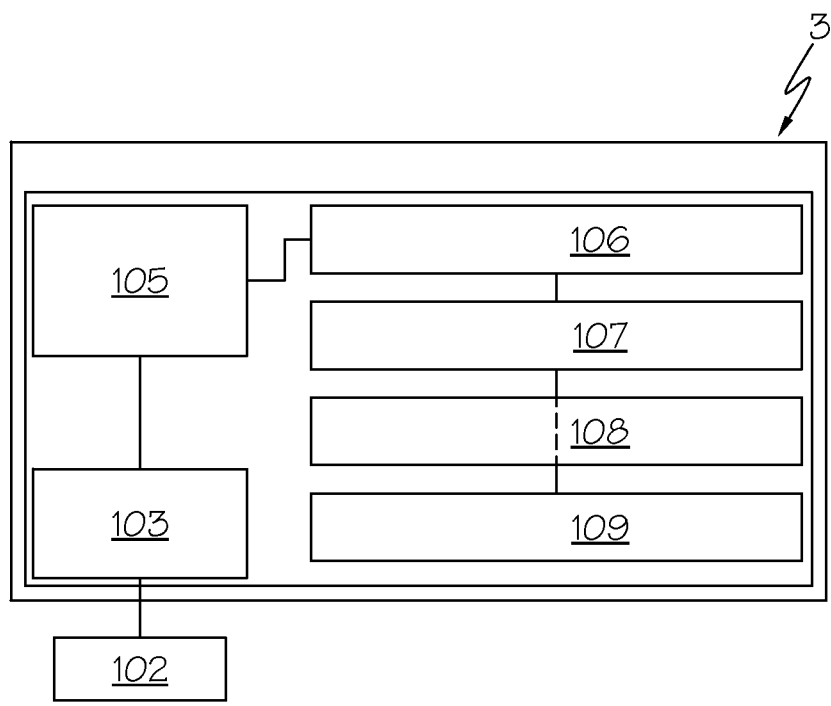
FIG. 14 depicts a schematic diagram illustrating functional entities of a second exemplary configuration of a processing unit of a system according to one or more embodiments of the invention.

Reference is made to FIG. 14 illustrating a schematic diagram of the functional layout of a second exemplary configuration of the microfluidic processing unit 3 of the system 1 according to one or more embodiments of the invention. In order to avoid unnecessary repetitions only differences with respect to the first exemplary configuration of FIG. 13 are explained and otherwise reference is made to explanations made in connection with FIG. 13.

Accordingly, in the processing unit 3, the functional entity mixing and incubation 107 is connected to another functional entity denoted as "sample and reagent R1 dosing 106" used for dosing the sample and reagent of a first set of reagents R1 and yet another functional entity denoted as "reagent R2/3 dosing 109" used for dosing reagent of second and third sets of reagents R2/3 different from the first set of reagents R1 as predefined by the functional entity sample and reagent R1 dosing 106. The analytical unit 108 including a detector is used for detecting a reaction result of the sample/reagent mixture obtained for analyzing the sample based on the detected reaction result.

Figure 15:
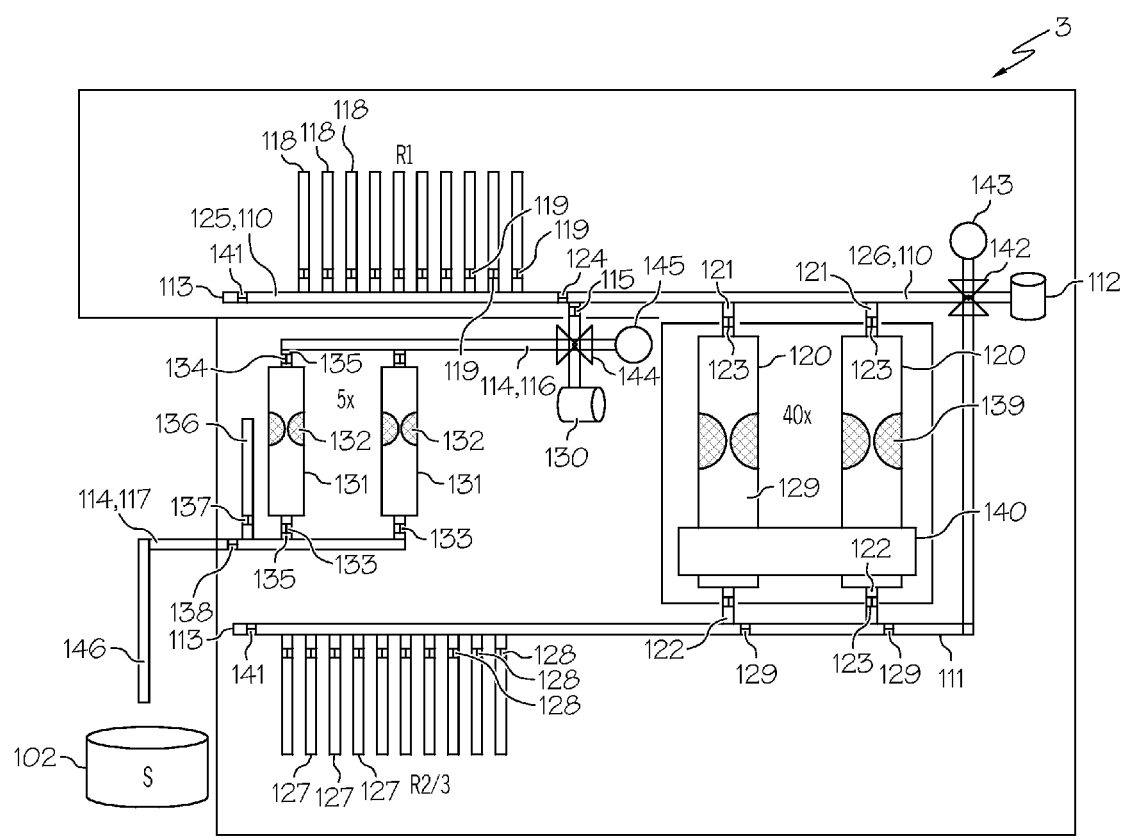
FIG. 15 depicts a schematic diagram depicting an exemplary embodiment of the processing unit of FIG. 14.

With particular reference to FIG. 15, an exemplary embodiment of the second configuration of the processing unit 3 of FIG. 14 is explained.

Accordingly, the microfluidic processing unit 3 includes a plurality of channels and chambers through which samples and reagents can be transported with a view of analyzing the liquid samples. The cross-sectional dimension of the channels and chambers typically is on the order of micrometer-scale and, e.g., may be as small as 1 µm to 500 µm. The processing unit 3 contains gaseous system fluid, e.g. air, or alternatively a combination of gaseous and liquid system fluid so that samples, reagents, and any other fluid of interest can be transported through the channels and chambers by generating a negative or positive (atmospheric) pressure therein.

Stated more particularly, the microfluidic processing unit 3 includes a first main channel 110 and a second main channel 111. One end of each of the main channels 110, 111 is provided with a vent 113 to let ambient air pass into the processing unit 3. The other end of the second main channel 111 is fluidically connected to the first main channel 110. The other end of the first main channel 110 is connected to a main pump 112. By use of the main pump 112, positive or negative (atmospheric) pressures can be generated in both the first main channel 110 and the second main channel 111.

In the microfluidic processing unit 3, liquid samples can be transported to the first main channel 110 through a sample channel 114 which can be connected to the sample vessel 102 containing liquid sample S. One end of the sample channel 114 is fluidically connected to the first main channel 110 while the other end thereof is fluidically connected to a sample intake 146 which can be used for aspirating the sample from the sample vessel 102. The sample channel 114 is equipped with a first freeze/thaw-valve 115 so as to enable or block sample flow from the sample channel 114 to the first main channel 110. The first freeze/thaw-valve 115 is located adjacent to the opening of the sample channel 114 where the sample channel 114 opens into the first main channel 110.

The microfluidic processing unit 3 further comprises a plurality of first reagent channels 118 for supplying a first set of reagents R1 to the first main channel 110. Each of the first reagent channels 118 is connected to first reagent vessels (not shown) containing reagents of the first set of reagents R1 for reacting with the liquid samples. The first set of reagents R1 contained in the first reagent vessels may include one or plural reagents different with respect to each other dedicated to a predefined first assay adapted for analyzing one or more analytes in the samples S. Each of the first reagent channels 118 opens into the first main channel 110 and is equipped with a second freeze/thaw-valve 119 so that reagent flow from the first reagent channels 118 to the first main channel 110 can be enabled or blocked. The second freeze/thaw-valves 119 are located adjacent to an opening where the first reagent channels 118 open into the first main channel 110.

The microfluidic processing unit 3 further includes a plurality of reaction chambers 120 for reaction of liquid sample and reagent to take place. The reaction chambers 120 may be embodied, e.g., as flow-through cuvettes. Each of the reaction chambers 120 is interconnected between the first main channel 110 and the second main channel 111 through a first reaction chamber port 121 connecting the reaction chamber 120 to the first main channel 110 and a second reaction chamber port 122 connecting the reaction chamber 120 to the second main channel 111. Each of the ports 121, 122 is equipped with a third freeze/thaw-valve 123 so as to enable or block fluid flow between the reaction chamber 120 and the first and second main channels 110, 111, respectively. Each of the reaction chambers 120 are further equipped with plural cam-like (reaction chamber) projections 139 which reduce an inner diameter of the reaction chamber 120. The projections 139 are adapted for mixing fluid within the reaction chambers 120 when performing a reciprocating fluid movement caused by positive or negative pressures generated by the main pump 112.

In the processing unit 3, a number of, e.g. forty, reaction chambers 120 may be used which are in parallel arrangement with respect to each other. The reaction chambers 120 are embodied as incubation chambers for incubating sample/reagent mixtures contained therein and thus are adapted for keeping sample/reagent mixtures at one or more predefined temperatures during one or more time intervals for enabling reaction between sample and one or more reagents to take place.

As can be taken from FIG. 15, the first main channel 110 is equipped with a fourth freeze/thaw-valve 124 which is located between the vent 113 and the main pump 112. The fourth freeze/thaw-valve 124 partitions the first main channel 110 into a vent-sided portion 125 and a pump-sided portion 126 thereof. Each of the first reagent channels 118 communicates with the vent-sided portion 125 of the first main channel 110. The sample channel 114 communicates with the pump-sided portion 126 of the first main channel 110, wherein an opening where the sample channel 114 opens into the first main channel 110 is located adjacent to the fourth freeze/thaw valve 124 of the first main channel 110 with the first freeze/thaw valve 115 of the sample channel 114 being located adjacent to the fourth freeze/thaw valve 124. In addition, the first reaction chamber ports 121 communicate with the pump-sided portion 126 of the first main channel 110.

The processing unit 3 further includes a plurality of second reagent channels 127 for supplying reagents of a second and third set of reagents R2/R3 to the second main channel 111. The second reagent channels 127 are connected to second and third reagent vessels (not shown). The second and third reagent vessels contain reagents of the second and third set of reagents R2/R3 for reacting with the liquid samples which are different from the first set of reagents R1 contained in the first reagent vessels. The second and third sets of reagents R2, R3 contained in the second and third reagent vessels may include one or plural reagents different with respect to each other dedicated to the predefined first assay or to a predefined second assay adapted for analyzing one or more analytes in the samples S.

Each of the second reagent channels 127 communicates with the second main channel 111 and is equipped with a fifth freeze/thaw valve 128 so as to enable or block reagent flow from the second reagent channels 127 to the second main channel 111. Each of the fifth freeze/thaw valves 128 of the second reagent channels 127 is located adjacent to an opening where the second reagent channels 127 open into the second main channel 111.

The second main channel 111 is equipped with a plurality of sixth freeze/thaw valves 129 according to the number and in association with each of the reaction chambers 120. These sixth freeze/thaw valves 129 are arranged in-between an opening where the second reaction chamber port 122 of the associated reaction chamber 120 opens into the second main channel 111 and the main pump 112. Each of these sixth freeze/thaw valves 129 is located adjacent to the opening of the second reaction chamber port 122. Otherwise, each of the third freeze/thaw valves 123 of the second reaction chamber port 122 is located adjacent to the sixth freeze/thaw valve 129 of the second main channel 111.

The processing unit 3 further includes an auxiliary pump 130 which is connected to the sample channel 114 for generating a negative or positive pressure therein. The sample channel 114 is connected to a plurality of mixing chambers 131 through first and second mixing chamber ports 134, 133. In the processing unit 3, a number of, e.g., five mixing chambers 131 may be envisaged which are arranged in parallel arrangement with respect to each other. The mixing chambers 131 partition the sample channel 114 into a first sample channel portion 116 and a second sample channel portion 117 thereof. The first mixing chamber ports 134 of the mixing chambers 131 communicate with the first sample channel portion 116 while the second mixing chamber ports 133 communicate with the second sample channel portion 117. The mixing chamber ports 133, 134 are equipped with a seventh freeze/thaw valve 135 so as to enable or block sample flow between each of the mixing chambers 131 and the sample channel 114. Furthermore, each of the mixing chambers 131 is equipped with plural cam-like (mixing chamber) projections 132 projecting towards each other to reduce an inner diameter of the mixing chamber 131. The projections 132 are adapted for mixing fluid within the mixing chamber 131 when performing a reciprocating fluid movement caused by positive or negative pressures generated by the auxiliary pump 130.

The processing unit 3 further includes a diluting fluid channel 136 for supplying diluting fluid for diluting the liquid samples. The diluting fluid channel 136 is connected to a diluting fluid vessel (not shown) containing fluid such as water for diluting the samples. The diluting fluid channel 136 communicates with the sample channel 114 and is equipped with an eighth freeze/thaw valve 137 located adjacent to an opening where the diluting fluid channel 136 opens into the sample channel 114. Furthermore, the sample channel 114 is equipped with a ninth freeze/thaw valve 138 located in-between an opening where the diluting fluid channel 136 opens into the sample channel 114 and the sample vessel 102. The ninth freeze/thaw valve 138 of the sample channel 114 is located adjacent to the eighth freeze/thaw valve 137 of the diluting fluid channel 136. Accordingly, by use of the auxiliary pump 30, sample can be drawn into the sample channel 114, and, can be diluted with diluting fluid without affecting fluid manipulation in the first and second main channels 110, 111 and reaction chambers 120.

In the processing unit 3, the first and second main channels 110, 111 are further equipped with tenth freeze/thaw valves 141 close to the vents 113 so that the vent-sided end of the first and second main channels 110, 111 can be closed.

The processing unit 3 further includes a main wash unit 143 connected to the first and second main channels 110, 111 by means of first wash unit valve 142 which, e.g., may be embodied as two-way valve. The main wash unit 143 can be used for supplying washing fluid to the first and second main channels 110, 111 so as to wash the main channels 110, 111 and the reaction chambers 120. The first wash unit valve 142 can be used to connect or disconnect the main wash unit 143 to/from the main channels 110, 111.

The processing unit 3 further includes an auxiliary wash unit 145 connected to the sample channel 114 by means of second wash unit valve 144 which, e.g., may be embodied as two-way valve. The auxiliary wash unit 145 can be used for supplying washing fluid to the sample channel 114 so as to wash the sample channel 114 and mixing chambers 131. The second wash unit valve 144 can be used to connect or disconnect the auxiliary wash unit 145 to/from the sample channel 114.

The analytical unit 2 includes one detector 140 for detecting a reaction product of sample/reagent mixtures contained in the reaction chambers 120. Accordingly, detector 140 is used for the detection of reaction products in all of the reaction chambers 120. The detector 140 may, e.g., be embodied as scanning optical detector adapted to receive an optical signal such as a fluorescence signal emitted by the sample/reagent mixtures contained in the reaction chambers 120.

In the processing unit 3 according to one or more embodiments of the invention, each of the freeze/thaw valves is permanently cooled by means of cold contacts contacting the channels ("cold fingers"), e.g., to have a temperature of $-30°$ C. so that aqueous fluid arriving at a freeze/thaw valve is quickly frozen and generates an ice plug blocking the fluid flow at the position of the freeze/thaw valve. The cold contacts may be cooled, e.g., by thermoelectric devices such as Peltier elements utilizing the Peltier effect. As is known to the skilled persons, when passing electric current through the Peltier element and depending on the direction of current applied, it functions as heat sink which adsorbs heat thereby to cool the contact. Otherwise, the ice plug of the freeze/thaw valve can be melted by locally introducing thermal energy using a heating means, e.g., by means of a laser beam which is directed to the freeze/thaw valve or by generating Ohmic heat using a resistor.

While not shown in FIG. 15, the analytical unit 2 further includes a controlling unit which, e.g., may be embodied as programmable logic controller running a computer-readable program provided with instructions to perform operations in accordance with the automated analysis of the samples. The controlling unit is connected to the components which require control and/or provide information. Stated more particularly, the controlling unit receives information from the different components of the processing unit 3, and generates and transmits corresponding control signals. In that, the controlling unit is electrically connected to the main and auxiliary pumps 112, 130, the main and auxiliary wash units 143, 145, the first and second wash unit valves 142, 144 and to each of the freeze/thaw valves in order to cool the freeze/thaw valves and to actuate the heating means to open the freeze/thaw valves. Particularly, the controlling unit is set up to control intake of samples and transport of the samples to the reaction chambers 120. It is yet further set up to control mixing and diluting of the samples with diluting fluid by use of the mixing chambers 131. It is yet further set up to control intake of reagents and transport of the reagents to the reaction chambers 120. It is yet further set up to control reaction of the samples with one or more reagents to obtain reaction products. Moreover, it is yet further set up to control analysis of the samples based on the reaction products obtained by means of the detector 140.

In above processing unit 3, in case of having adjacent freeze/thaw valves, the freeze/thaw valves are being located exactly at an intersection (i.e. corner) of communicating fluid channels. Hence, fluids can be provided in one fluid channel without having a gap in-between so that, e.g., sample and reagent may be attached to each other. Adjacent freeze/thaw valves, however, are just a preferred option. Alternatively, freeze/thaw valves of communicating fluid channels may also be separated from the intersection of the fluid channels. In the latter case, a gaseous or liquid system fluid filled gap may be present in-between fluids provided in one fluid channel.

With particular reference to FIGS. 16A to 16G an exemplary method of analyzing a liquid sample using the structural layout of FIG. 15 is explained. In FIGS. 16A to 16G, in order to simplify the drawings, a first main channel 110-sided end portion of the sample channel 114 is depicted only. It, however, is to be understood that the sample channel 114 includes all the components shown in FIG. 15.

Figure 16A:
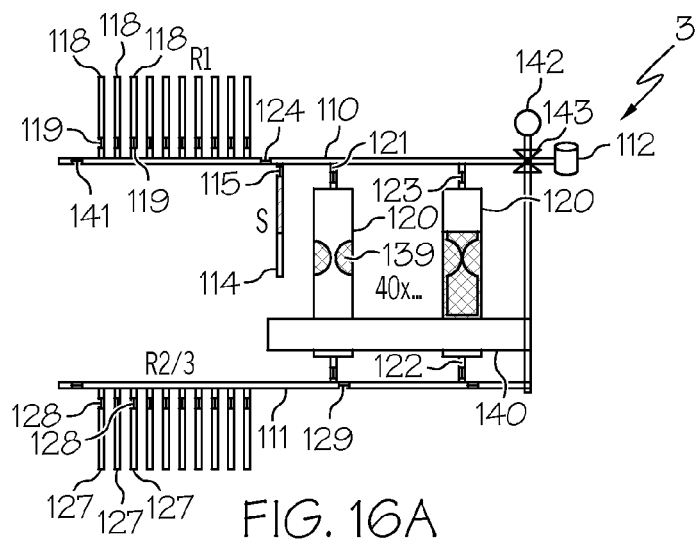
FIGS. 16A-16G illustrate an exemplary method of processing a liquid sample using the processing unit of FIG. 15.

In a first step ("sample intake"), a desired volume of sample S is sucked from the sample vessel 102 into the sample channel 114 by generating a negative pressure by the main pump 112 during a predefined time interval. The first freeze/thaw valve 115 of the sample channel 114 is used to stop the sample S at the dead end of the sample channel 114. The sample S is transiently kept there (i.e. registered) for later use. Due to the location of the first freeze/thaw valve 115 at the dead end of the sample channel 114, formation of air bubbles can be avoided in case the sample is drawn into the first main channel 110 (FIG. 16A).

Figure 16B:
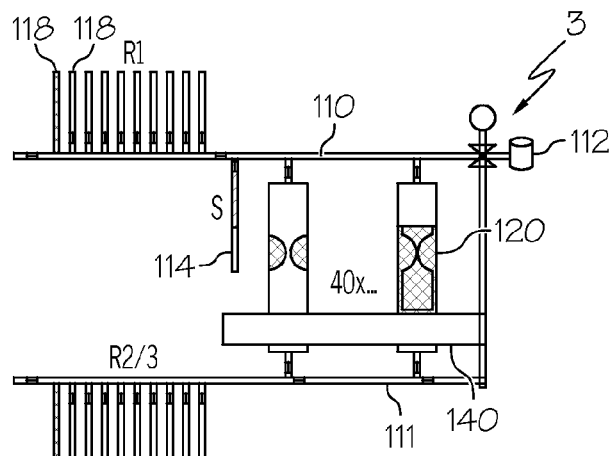

In a second step ("reagent R1 dosing"), a predefined volume of one reagent selectively chosen of the first set of reagents R1 is sucked into the first main channel 110. For that purpose, the second freeze/thaw valve 119 of the selected one of the first reagent channels 118 (e.g. the marked outermost left one) containing reagent of the first set of reagents R1 of the corresponding assay to be performed with sample S is opened. Then, a negative pressure is generated in the first main channel 110 by the main pump 112 acting on the first reagent channel 118 while having the second freeze/thaw valve 119 open to thereby suck reagent into the first main channel 110. In that, gaseous system fluid based (or gaseous and liquid system fluid based pumping) of reagent is performed by use of the main pump 112. After a predetermined period of time necessary for dosing a desired volume of reagent, the second freeze/thaw valve 119 is closed by sufficiently cooling the second freeze/thaw valve 119 to generate an ice plug so as to provide a predefined volume of reagent in the first main channel 110. Accordingly, opening or closing the second freeze/thaw valve 119 allows for a precise dosing of reagent. In the first main channel 110, the fourth freeze/thaw valve 124 is used to stop the reagent without air bubble right before the sample port, that is to say, right before the opening of the sample channel 114. The fourth freeze/thaw valve 124 thus allows for precisely keeping reagent at a predefined location (FIG. 16B).

Figure 16C:
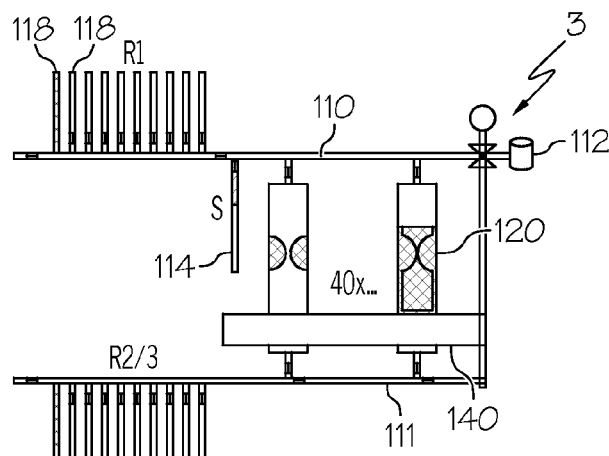

In a third step ("sample dosing"), a predefined volume of sample S is sucked into the first main channel 110. For that purpose, the first freeze/thaw valve 115 of the sample channel 114 is opened and a negative pressure is generated in the first main channel 110 by the main pump 112 acting on the sample channel 114 while having the first freeze/thaw valve 115 open thereby to suck (draw) the sample S into the first main channel 110. In that, gaseous system fluid based (or gaseous and liquid system based) pumping of sample S is performed by use of the main pump 112. After a predetermined period of time necessary for dosing a desired volume of the sample S, the first freeze/thaw valve 115 of the sample channel 114 is closed by sufficiently cooling the first freeze/thaw valve 115 to generate an ice plug so as to provide a predefined volume of sample S in the first main channel 110. The sample S is placed right before the reagent ice plug of the fourth freeze/thaw valve 124 of the first main channel 110 without air bubble in-between the sample S and the fourth freeze/thaw valve 124. Hence, both reagent and sample S can be placed in the first main channel 110 separated by the fourth freeze/thaw valve 124 without having an air bubble in-between (FIG. 16C).

Figure 16D:
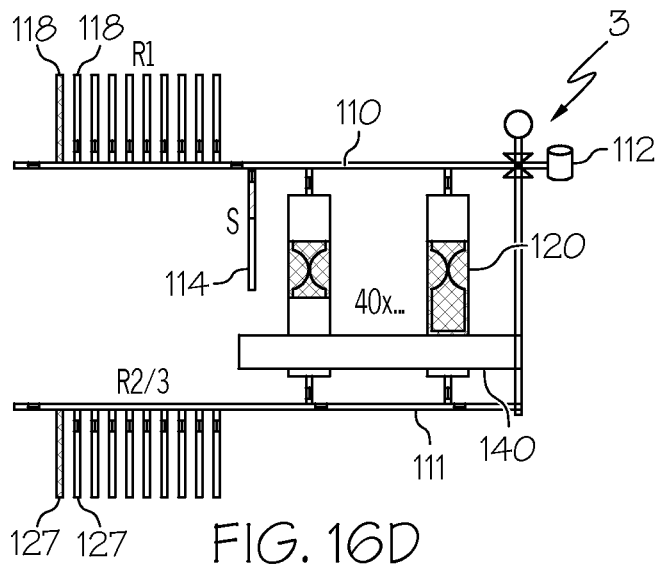

In a fourth step ("move and mix"), sample S and reagent both are sucked into one of the reaction chambers 120 (e.g. the outermost left one). For that purpose, the fourth freeze/thaw valve 124 of the first main channel 110 is opened and a negative pressure is generated in the first main channel 110 by the main pump 112 while the third freeze/thaw valves 123 of the reaction chamber 120 are kept open so that sample S and reagent can be sucked into the reaction chamber 120. The reaction mix is then moved to the centre of the reaction chamber 120, followed by closing the third freeze/thaw valves 123 of the reaction chamber ports 121, 122 by sufficiently cooling the third freeze/thaw valves 123 to generate ice plugs. Then, mixing is performed in the reaction chamber 120 by means of the main pump 112 using the projections 139 (FIG. 16D).

While not shown in the figures, in case of providing for another (second) pump connected to the second main channel 111, mixing of the fluids can also be performed under action of both pumps. Alternatively or additionally, reagent and sample S could also be mixed in the pump-sided portion 126 of the first main channel 110 by generating negative and positive pressures by means of the main pump 112.

Figure 16E:
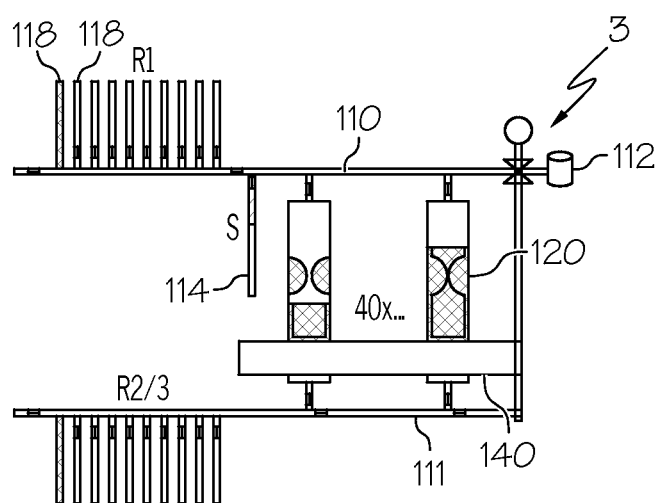

In a fifth step ("reagent R2/3 dosing"), a pre-defined volume of reagent of the second and third sets of reagents R2/R3 different from the first set of reagents R1 is sucked into the second main channel 111. For that purpose, the reaction mix obtained is moved to the second main channel 111-sided end of the reaction chamber 120. Then, the fifth freeze/thaw valve 128 of one of the second reagent channels 127 (e.g. the outermost left one) containing reagent of the corresponding assay to be performed with sample S is opened. Then, a negative pressure is generated in the second main channel 111 by the main pump 112 acting on the selected second reagent channel 127 having the fifth freeze/thaw valve 128 open to thereby suck reagent R2 into the second main channel 111. After a predetermined period of time necessary for dosing a desired volume of reagent, the fifth freeze/thaw valve 128 is closed by sufficiently cooling the fifth freeze/thaw valve 128 to generate an ice plug so as to provide a predefined volume of reagent in the second main channel 111. In the second main channel 111, the sixth freeze/thaw valve 129 is used to stop the reagent without having an air bubble in front of the second reaction chamber port 122. This procedure can analogously be repeated for another reagent of the first and second sets of reagents R2, R3 (FIG. 16E).

Figure 16F:
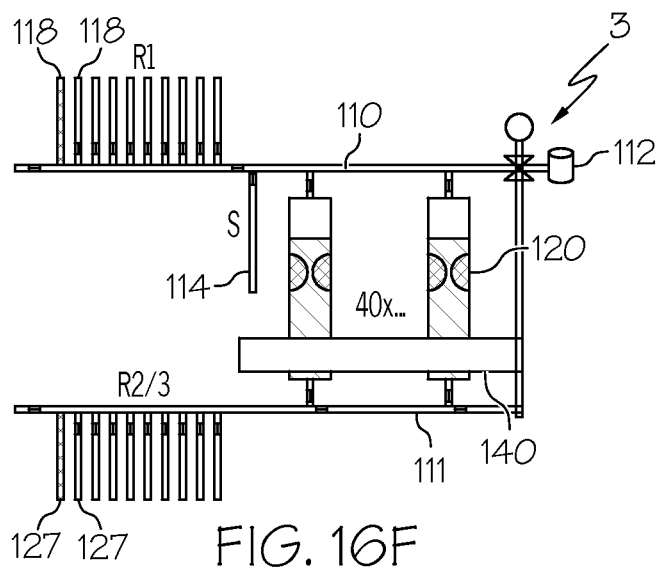

In a sixth step ("reagent R2/3 add and mix"), the reagent is drawn (sucked) into the corresponding reaction chamber 120. For that purpose, the third freeze/thaw valve 123 of the second reaction chamber port 122 is opened. Then, negative pressure is generated by the main pump 112 so that the reagent can be sucked into the reaction chamber 120. The reaction mix is moved to the centre of the reaction chamber 120, followed by closing the third freeze/thaw valves 123 of the reaction chamber ports 121, 122. Then, mixing within the reaction chamber 120 by means of the main pump 112 using the projections 139 is performed (FIG. 16F).

While not shown in the figures, in case of providing for another (second) pump connected to the second main channel 111, mixing of the fluids can be performed under action of both pumps.

In a seventh step ("washing and scanning"), by use of the washing unit 143, the contents of one of the reaction chambers 120 is withdrawn, followed by cleaning the reaction chamber by a dedicated cleaning procedure using washing fluid. Likewise, all channels can be washed by the washing fluid. In the cleaning procedure, e.g., a pressure-driven film cleaning with sequential use of cleaning fluid, water and pressure for drying can be performed.

Figure 16G:
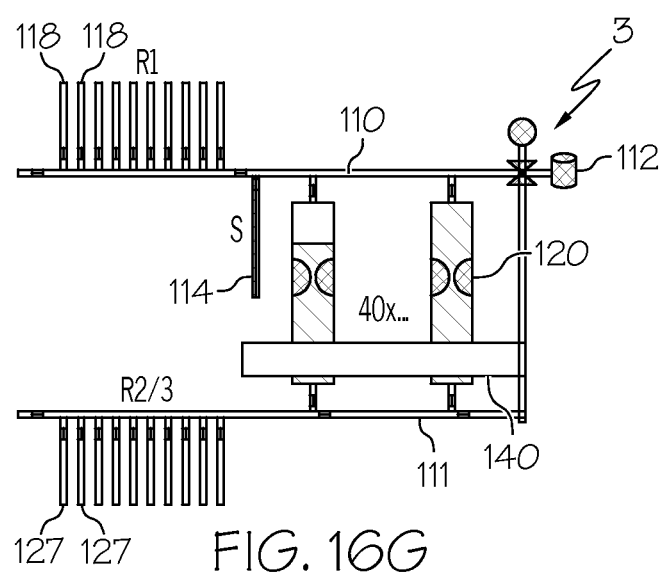

Furthermore, in that step, the detector 140 of the analytical unit continuously scans the reaction chambers 120 in order to detect reaction products in view of analyzing the sample S based on the reaction result obtained (FIG. 16G).

Sample S can be diluted by diluting fluid supplied by the diluting fluid channel 136 using the auxiliary pump 130. Stated more particularly, while not detailed in above method, sample S can also be mixed with diluting fluid within the mixing chambers 131 using the projections 132 by generating a reciprocating movement of the sample S using the auxiliary pump 130. Accordingly, manipulative steps of the sample S within the sample channel 114 are decoupled from manipulative steps within the main channels 110, 111 and reaction chambers 120, respectively.

In above exemplary method of analyzing a liquid sample, sample S and reagent of the first set of reagents R1 are commonly sucked into one of the reaction chambers 120, followed by adding another reagent of the second and third sets of reagents R2/R3. Due to adjacent freeze/thaw valves, there is no gap in-between sample and reagent of the first set of reagents R1. Alternatively, a gap may be present in-between sample and reagent of the first set of reagents R1. Yet alternatively, sample S and reagent(s) may also be independently (separately) transported to the reaction chamber 120. In that, in a first option, first sample S is transported to the reaction chamber 120, followed by transporting reagent of the first set of reagents R1 to the reaction chamber 120, optionally followed by transporting reagent of the second set of reagents R2 and optionally followed by transporting reagent of the third set of reagents R3 to the reaction chamber 120. In a second option, first reagent of the first set of reagents R1 is transported to the reaction chamber 120, followed by transporting the sample S to the reaction chamber 120, optionally followed by transporting reagent of the second set of reagents R2 and optionally followed by transporting reagent of the third set of reagents R3 to the reaction chamber 120. In a third option, first reagent of the first set of reagents R1 is transported to the reaction chamber 120, optionally followed by transporting reagent of the second set of reagents R2 and optionally followed by transporting reagent of the third set of reagents R3 to the reaction chamber 120, and followed by transporting the sample S to the reaction chamber 120.

The planar/linear arrangement of the processing unit 3 enables an easy and cost-effective manufacturing thereof. Due to parallel processing of samples, a comparably high throughput is enabled. Furthermore, due to first and second reagent channels, carry-over of different reagents can be avoided. Decoupling of sample preparation and sample analysis can be reached by using only two separate pumps.

Figure 17:
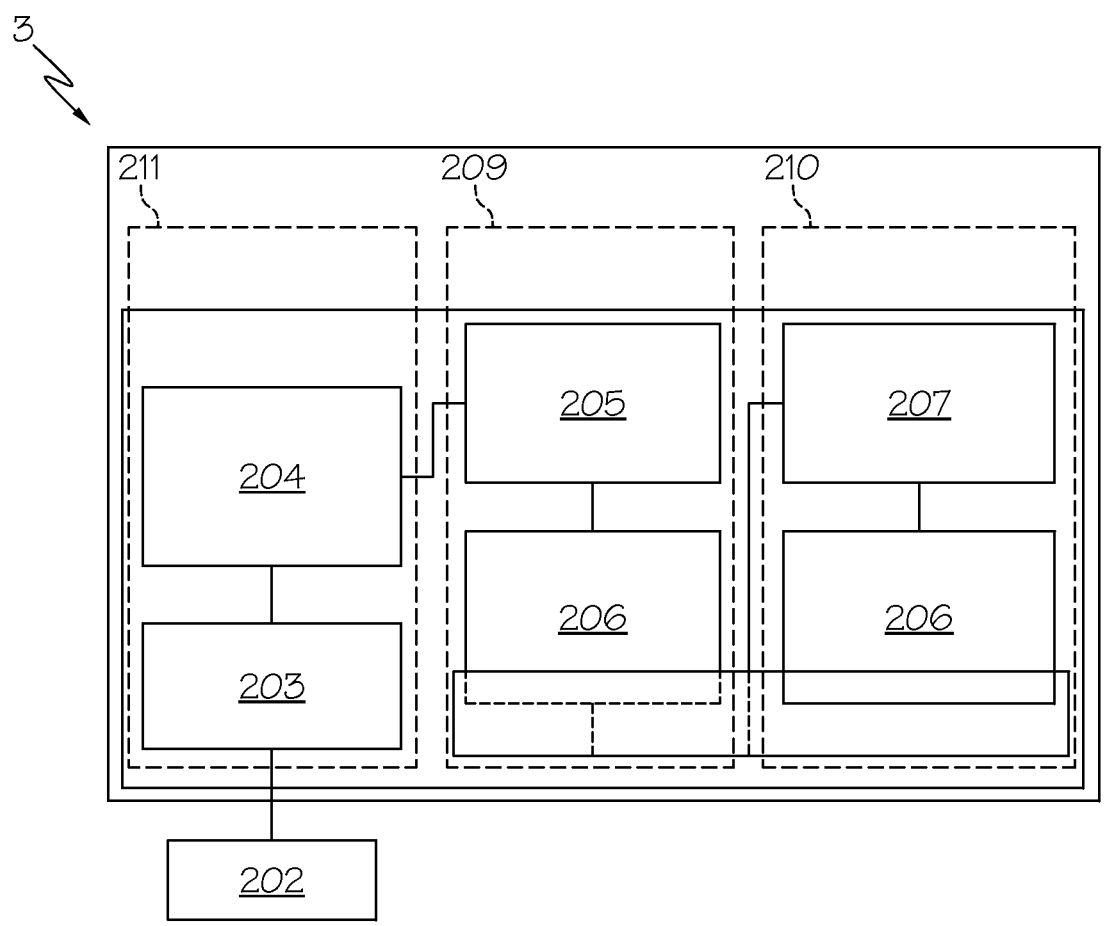
FIG. 17 depicts a schematic diagram illustrating functional entities of a third exemplary configuration of a processing unit of a system according to one or more embodiments of the invention.

Referring to FIG. 17, a schematic diagram illustrating the functional layout of a third exemplary configuration of the processing unit 3 according to one or more embodiments of the invention is explained.

Accordingly, a processing unit 3 for the processing of liquid samples provides functional segmentation for the decoupling of workflow steps and achieving an increased throughput. Any fluid (sample or sample/reagent mixture) is transported from one segment to the next one. The functional segments are serially arranged with respect to each other, wherein each segment has its own precise dosing pump.

Stated more particularly, the processing unit 3 includes a functional entity denoted as "sample aspiration 203" connectable to a sample vessel 202 which enables liquid sample contained in the sample vessel 202 to be drawn into the processing unit 3. The functional entity sample aspiration 203 is connected to another functional entity denoted as "sample register/pre-dilution 204" used for diluting the sample with diluting fluid and registering the sample. The functional entity sample register/pre-dilution 204 is connected to another functional entity denoted as "sample and reagent R1 dosing 205" used for dosing the sample and reagent of a first set of reagents R1. The functional entity sample and reagent R1 dosing 205 is connected to another functional entity denoted as "mixing and incubation 206" for mixing the sample with reagent of the first set of reagents R1 and incubating the sample/reagent mixture obtained in the reaction chamber for reaction to take place. The functional entity mixing and incubation 206 is connected to another functional entity denoted as "reaction mix and reagent R2/3 dosing 207" for dosing the reaction mix and dosing reagents of the second and third sets of reagents R2, R3. The functional entity reaction mix and reagent R2/3 dosing 207 is connected to another functional entity denoted as "mixing and incubation 206" used for mixing the mixture of sample and reagent of the first set of reagents R1 with reagent of the second and third set of reagents R2/R3 and incubating the sample/reagent mixture obtained for reaction to take place. Another functional entity denoted as "analytical unit 208" which includes one detector for detecting a reaction product of the sample/reagent mixture obtained is used for analyzing the sample based on the detected reaction product.

In the processing unit 3, a first segment 209 includes the entity sample and reagent R1 dosing 205 and the entity mixing and incubation 206, a second segment 210 includes the entity reaction mix and reagent R2/3 dosing 207 and the entity mixing and incubation 206, and a third segment 211 includes the entity sample aspiration 203 and the entity sample register/pre-dilution 204.

Figure 18:
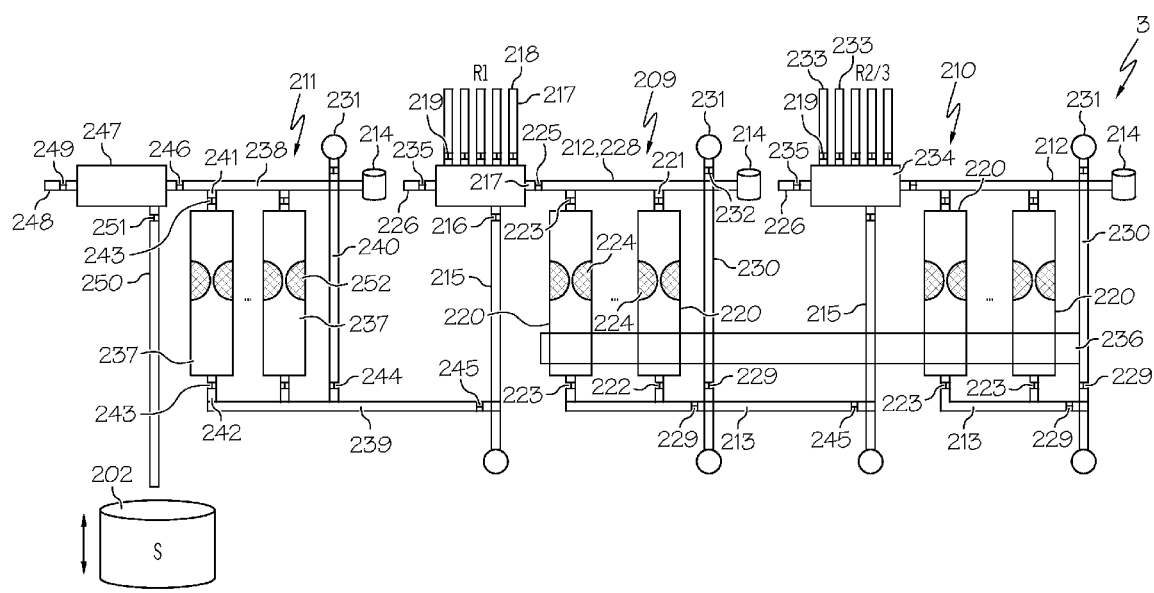
FIG. 18 depicts a schematic diagram depicting an exemplary embodiment of the processing unit of FIG. 17.

With particular reference to FIG. 18 an exemplary embodiment of the third exemplary configuration of the processing unit 3 of FIG. 17 is explained, which processing unit includes the three segments 209-211.

The first segment 209 includes a first main channel 212 and a second main channel 213. The second main channel 213 is connected to the first main channel 212 through interconnect channel 230. The first main channel 212 is provided with a vent 226 and connected to a pump 214. By use of the pump 214, positive or negative (atmospheric) pressures can be generated both in the first and second main channels 212, 213, respectively.

Liquid samples can be transported to the first main channel 212 through sample channel 215 which is connected to the first segment 209 and opens into a first reagent dosage chamber 217. The sample channel 215 is equipped with a first freeze/thaw-valve 216 so as to enable or block sample flow from the sample channel 215 to the first reagent dosage chamber 217. The first freeze/thaw-valve 216 of the sample channel 215 is located adjacent to the opening of the sample channel 215 into the first reagent dosage chamber 217.

The first segment 209 further comprises a plurality of first reagent channels 218 for supplying reagents of a first set of reagents R1 to the first reagent dosage chamber 217. Each of the first reagent channels 218 is connected to first reagent vessels (not shown) containing reagents of the first set of reagents R1 for reacting with the liquid samples. The reagents of the first set of reagents R1 contained in the first reagent vessels may include one or plural reagents which may be different with respect to each other and can be related to a first assay dedicated to determine one or more analytes in the samples. Each of the first reagent channels 218 opens into the first reagent dosage chamber 217 and is equipped with a second freeze/thaw-valve 219 so that reagent flow from the first reagent channels 218 to the first reagent dosage chamber 217 can be enabled or blocked. The second freeze/thaw-valves 219 are located adjacent to an opening where the first reagent channels 218 open into the first reagent dosage chamber 217.

The first segment 209 further comprises a plurality of reaction chambers 220 for reaction of liquid sample and one or more reagents to take place which, e.g., may be embodied as flow-through cuvettes. Each of the reaction chambers 220 is interconnected between the first main channel 212 and the second main channel 213 through a first reaction chamber port 221 connecting the reaction chamber 220 to the first main channel 212 and a second reaction chamber port 222 connecting the reaction chamber 220 to the second main channel 213. Each of the reaction chamber ports 221, 222 is equipped with a third freeze/thaw-valve 223 so as to enable or block fluid flow between the reaction chamber 220 and the first and second main channels 212, 213, respectively. Each of the reaction chambers 220 is further equipped with plural cam-like projections 224 which reduce an inner diameter of the reaction chamber 220 and are adapted for mixing fluid when performing a reciprocating fluid movement caused by positive or negative pressures generated by the pump 214. The reaction chambers 220 are embodied as incubation chambers for incubating sample/reagent mixtures contained therein. The reaction chambers 220 are in parallel arrangement with respect to each other.

The first main channel 212 is further equipped with a fourth freeze/thaw-valve 225 which partitions the first main channel 212 into a vent-sided portion 227 and a pump-sided portion 228. The first reagent channels 218 and the sample channel 215 communicate with the first reagent dosage chamber 217 which is on the vent-sided portion 227 of the first main channel 212.

The second main channel 213 of the first segment 209 is connected to the second reagent dosage chamber 234 of the second segment 210 by sample channel 215. At the crossing between the second main channel 213 and the interconnect channel 230, each of these channels is equipped with a fifth freeze/thaw valve 229.

The processing unit 3 further includes a wash unit 231 connected to the first and second main channels 212, 213 by means of first wash unit valve 232. The wash unit 231 can be used for supplying washing fluid to the first and second main channels 212, 213 so as to wash the main channels 212, 213 and the reaction chambers 220. The first wash unit valve 232 can be used to connect or disconnect the main wash unit 231 to/from the main channels 212, 213.

In the first segment 209, the first main channel 212 is equipped with a sixth freeze/thaw valve 235 close to the vent 226 so that the vent-sided end of the first main channel 212 can be closed.

The second segment 210 is of largely similar construction to the first segment 209. In order to avoid unnecessary repetitions, only differences with respect to the first segment 209 are explained and otherwise reference is made to explanations relating to the first segment 209. Accordingly, the second segment 210 is provided with a plurality of second reagent channels 233 for supplying reagents of second and third sets of reagents R2/R3 to the second reagent dosage chamber 234. Each of the second reagent channels 233 is connected to second reagent vessels (not shown) containing reagent of the second set of reagents R2 and reagent of the third set of reagents R3 for reacting with the liquid samples. Each of the second reagent channels 233 opens into the second reagent dosage chamber 234 and is being equipped with a second freeze/thaw-valve 219 so that reagent flow from the second reagent channels 233 to the second reagent dosage chamber 234 can be enabled or blocked. The second freeze/thaw-valves 219 of the second reagent channels 233 are located adjacent to an opening where the second reagent channels 233 open into the second reagent dosage chamber 234.

The second main channel 213 of the first segment 209 is connected to the sample channel 215 of the second segment 210. Hence, each of the second reaction chamber ports 222 of the reaction chambers 220 of the first segment 209 is connected to the sample channel 215 of the second segment 210 so that sample and/or sample/reagent mixture can be transported from the reaction chambers 220 of the first segment 209 to the reaction chambers 220 of the second segment 210. The second segment 210 includes a separate pump 214.

The processing unit 3 yet further includes a detector 236 which is part of an analytical unit (not shown) for detecting a reaction product of sample/reagent mixtures contained in the reaction chambers 220. Accordingly, one detector 236 is used for the detection of reaction products in the reaction chambers 220 of the first and second segments 209, 210, respectively.

The third segment 211 includes plural mixing and registering chambers 237 interconnected between a first sample channel portion 238 and a second sample channel portion 239 through first and second mixing chamber ports 241, 242, respectively. In each mixing and registering chamber 237, the first mixing chamber port 241 connects the mixing and registering chamber 237 to the first sample channel portion 238 and the second mixing chamber port 242 connects the mixing and registering chamber 237 to the second sample channel portion 239. Each of the mixing chamber ports 241, 242 is provided with a seventh freeze/thaw valve 243. The plural mixing and registering chambers 237 are in parallel arrangement with respect to each other. Each of the mixing and registering chambers 237 is provided with projections 252, which reduce an inner diameter of the mixing and registering chambers 237 and are adapted for mixing fluid when performing a reciprocating fluid movement caused by positive or negative pressures generated by the pump 214 of the third segment 211. Otherwise, the mixing and registering chambers 237 may serve for registering of fluid.

The first sample channel portion 238 and the second sample channel portion 239 are connected through interconnect channel 240 which is equipped with an eighth freeze/thaw valve 244 close to the crossing between the second sample channel portion 239 and the interconnect channel 240.

The first sample channel portion 238 opens into vent 248. In-between the vent 248 and the pump 214, the first sample channel portion 238 is connected to a sample dosage chamber 247 which is connected to the sample vessel 202 through sample intake 250. The sample intake 150 is equipped with a twelfth freeze/thaw valve 251 located at the opening where the sample intake 250 opens into the sample dosage chamber 247. The second sample channel portion 239 of the third segment 211 is connected to the sample channel 215 of the first segment 209 so that the second mixing chamber ports 242 of the mixing and registering chambers 237 are connected to the sample channel 215 of the first segment 209. The second sample channel portion 239 is provided with a ninth freeze/thaw valve 245 which is located adjacent to the opening where the second sample channel portion 239 opens into the sample channel 215 of the first segment 209.

The sample dosage chamber 247 is connected to a diluting fluid channel (not shown) for supplying diluting fluid for diluting liquid contained in the sample dosage chamber 247.

In the following, an exemplary method using the processing unit 3 is described. Accordingly, by use of pump 214 of the third segment 211, sample S is sucked through sample intake 250 into the sample dosage chamber 247. The sample then is transferred to one of the mixing and registering chambers 237. After mixing the sample with diluting fluid in the mixing and registering chamber 237 by performing a reciprocating movement generated by the pump 214, the sample then is transferred to the sample channel 215 of the first segment 209 via the second sample channel portion 239. The sample then is sucked into the first reagent dosage chamber 217 of the first segment 209 by use of the pump 214 of the first segment 209. After that, reagent of the first set of reagents R1 is transferred into the first reagent dosage chamber 217 by one of the first reagent channels 218. Then, the sample/reagent-mixture obtained is transferred into one of the reaction chambers 224 via the first main channel 212. The sample/reagent-mixture is mixed within the reaction chamber 224 performing a reciprocating movement caused by the pump 214. The sample/reagent-mixture then is transferred to the sample channel 215 of the second segment 210 via the second main channel 213. The sample/reagent-mixture then is sucked into the second reagent dosage chamber 234 by use of the pump 214 of the second segment 210. After that, optionally reagent of the second set of reagents R2 and optionally reagent of the third set of reagents R3 both of which are different from the first set of reagents R1 is transferred into the second reagent dosage chamber 234 by one of the second reagent channels 233. Then, the sample/reagent-mixture obtained is transferred into one of the reaction chambers 224 via the first main channel 212. The sample/reagent-mixture then is mixed in the reaction chamber 224 performing a reciprocating movement caused by the pump 214 of the second segment 210. A reaction product of the mixture then is determined using the detector 236. Based on the detected reaction product, the sample is analyzed using the analytical unit (not shown).

The various embodiments of the invention have many advantages over the prior art, inter alia, the following:

in the processing unit according to one or more embodiments, instead of concentrated reagents, non-concentrated reagents or reagents having low concentrations can be used (as a matter of fact some reagents cannot be concentrated);

a comparably large number (e.g. hundreds) of reagent channels can be connected to the first and/or second main channels;

no dilution effects of samples and reagents with liquid system fluid occur;

various volumes of reagents and/or samples can be predefined with flexibility;

bubble-free priming of sample and/or reagent is enabled;

in a processing unit according one or more embodiments, carry-over effects of samples and/or sample/reagent mixtures can be minimized;

in a processing unit according one or more embodiments, having first and second reagent channels, carry-over effects of various reagents can be minimized;

in a processing unit according one or more embodiments, due to using one reaction chamber for both reaction (incubation) and detection, variations when transferring the sample/reagent mixture obtained from one reaction chamber to another reaction chamber can be avoided;

one single detector can be used for plural reaction chambers of plural segments;

in case of using a scanning detector, end point and kinetic assays are enabled;

few moving part, thus avoiding frequent maintenance operations;

reagent vessels connected to the reagent channels are hermetically closed by the on/off valves, which prolongs stability (shelf-time) of the reagents;

using separate pumps, preparative sample manipulation (aspiration, dilution, mixing) can be decoupled from sample analysis;

only one sample intake is required for several tests to be performed;

low costs enable easy parallelization of the processing unit;

broad scalability; processing unit infrastructure can be shared by various components; and easy miniaturization of the processing unit (small sample volumes, small reagent volumes).

While particular embodiments and aspects of the present invention have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. A microfluidic processing unit for the automated processing of liquid samples, comprising:
    at least one first main channel and at least one second main channel connected to a pump for generating a negative or positive pressure therein;
    at least one sample channel for supplying liquid sample connectable to a sample vessel containing said liquid sample, said sample channel communicating with said first main channel and being equipped with an on/off valve;
    one or more reagent channels for supplying one or more reagents, said reagent channels being connectable to reagent vessels containing reagents for reacting with said liquid samples, each of said reagent channels communicating with said first or second main channel and being equipped with an on/off valve; and
    at least one reaction chamber in which a reaction between a sample and reagent can take place, said reaction chamber being connected to said first and second main channels via at least one on/off valve;
    wherein said first main channel is equipped with an on/off valve in-between a vent and said pump, wherein said one or more reagent channels communicate with a vent-sided portion of said first main channel and wherein said sample channel communicates with a pump-sided portion of said first main channel;
    wherein an opening where said sample channel opens into said first main channel is located adjacent to said on/off valve of said first main channel with said on/off-valve of said sample channel being located adjacent to said on/off valve of said first main channel;
    wherein said first reagent channels are connectable to first reagent vessels containing reagents for reacting with said liquid samples, each of said first reagent channels communicating with said vent-sided portion of said first main channel and being equipped with an on/off valve;
    wherein said second reagent channels are connectable to second reagent vessels containing reagents for reacting with said liquid samples, each of said second reagent channels communicating with said second main channel and being equipped with an on/off valve; and
    wherein said second main channel is equipped with one or more on/off valves in correspondence to the number of reaction chambers and associated thereto, wherein each of said on/off valves of said second main channel is arranged in-between an opening where said associated reaction chamber opens into said second main channel and said pump.

2. The processing unit according to claim 1, wherein each of said one or more on/off valves of said second main channel is located adjacent to said opening of said associated reaction chamber, wherein said on/off valve, via which said reaction chamber is being connected to said second main channel, is located adjacent to said on/off valve of said second main channel.

3. The processing unit according to claim 1, further comprising another pump connected to said sample channel which generates a negative or positive pressure therein.

4. The processing unit according to claim 1, in which said sample channel is connected to at least one mixing chamber via at least one on/off valve, each of said mixing chambers is provided with mixing means which mix fluid by performing a reciprocating fluid movement.

5. The processing unit according to claim 4, further comprising at least one diluting fluid channel for supplying diluting fluid, said diluting fluid channel being connectable to a diluting fluid vessel containing diluting fluid for diluting said liquid samples, said diluting fluid channel communicating with said sample channel and being equipped with an on/off valve.

6. A method for the automated processing of liquid samples, comprising:
    providing a processing unit according to claim 1;
    drawing a predefined volume of reagent into said vent-sided portion of said first main channel;
    drawing said liquid sample into said sample channel;
    drawing a predefined volume of said liquid sample into said pump-sided portion of said first main channel;
    drawing said predefined volume of liquid sample into said at least one reaction chamber;
    drawing said predefined volume of said reagent into said at least one reaction chamber to generate a sample/reagent mixture; and
    detecting a reaction product of said sample/reagent mixture contained in said at least one reaction chamber.

7. A microfluidic processing unit for the automated processing of liquid samples, comprising at least one set of first and second segments, each of which including:

at least one first and one second main channel connected to a pump for generating a negative or positive pressure therein;

at least one sample channel for supplying said liquid sample communicating with said first main channel and equipped with an on/off valve;

one or more reagent channels for supplying reagents, said reagent channels being connectable to reagent vessels containing reagents for reacting with said liquid samples, each of said reagent channels communicating with said first or second main channel and being equipped with an on/off valve;

at least one reaction chamber for reaction of sample and reagent to take place, said reaction chamber being connected to said first and second main channels via at least one on/off valve, wherein said second main channel of said first segment is being connected to said sample channel of said second segment; and a third segment comprising:
- a sample channel including one first sample channel portion and one second sample channel portion connected to a pump which generates a positive or negative pressure therein; and
- one or more mixing and registering chambers being connected to said first and second sample channel portions via at least one on/off valve,
- said first sample channel portion being connected to a sample vessel; and
- wherein said second sample channel portion of said third segment is connected to said sample channel of said first segment.

8. The processing unit according to claim 7, in which said first main channel is equipped with an on/off valve in-between said vent and said pump, wherein said one or more reagent channels communicate with a vent-sided portion of said first main channel and wherein said sample channel communicates with a pump-sided portion of said first main channel.

9. The processing unit according to claim 7, further comprising an analytical unit including one or more detectors for detecting reaction products contained in said reaction chambers of said first and second segments.

10. A method for the automated processing of liquid samples, comprising:

providing a processing unit according to claim 7;

drawing a predefined volume of first reagent into said vent-sided portion of said first main channel of said first segment;

drawing a predefined volume of said liquid sample into said sample channel of said first segment;

drawing a predefined volume of said liquid sample into said vent-sided portion of said first main channel of said first segment;

drawing said predefined volume of reagent into at least one reaction chamber of said first segment;

drawing said predefined volume of said liquid sample into said reaction chamber to generate a sample/reagent mixture;

drawing said sample/reagent mixture from said reaction chamber of said first segment to at least one reaction chamber of said second segment;

drawing a predefined volume of second reagent into said vent-sided portion of said first main channel of said second segment;

drawing said predefined volume of second reagent into said reaction chamber containing said sample/reagent mixture; and detecting a reaction product of said sample/reagent mixture contained in said reaction chamber.

\* \* \* \* \*

UNITED STATES PATENT AND TRADEMARK OFFICE
CERTIFICATE OF CORRECTION

PATENT NO. : 8,778,696 B2
APPLICATION NO. : 12/850949
DATED : July 15, 2014
INVENTOR(S) : Oliver Gutmann et al.

It is certified that error appears in the above-identified patent and that said Letters Patent is hereby corrected as shown below:

In the Specification

Col. 1, Line 64,
  "takes place, the reaction chamber being connected to the first" should read
  --take place, the reaction chamber being connected to the first--;

Col. 2, Line 16,
  "of which including: at least one first and one second main" should read
  --of which includes: at least one first and one second main--;

Col. 6, Line 22,
  "on/off valve of the first main channel with the on/off-valve of" should read
  --on/off valve of the first main channel with the on/off valve of--;

Col. 6, Line 25,
  "in the sample channel adjacent to the on/off-valve of the" should read
  --in the sample channel adjacent to the on/off valve of the--;

Col. 6, Line 33,
  "connected to first reagent vessels, each of which containing" should read
  --connected to first reagent vessels, each of which contains--;

Col. 6, Line 45,
  "channel by use of the on/off-valves. Each of the on/off valves" should read
  --channel by use of the on/off valves. Each of the on/off valves--;

Col. 6, Line 53,
  "each of which containing reagent for reacting with the liquid" should read
  --each of which contains reagent for reacting with the liquid--;

Signed and Sealed this
Nineteenth Day of May, 2015

Michelle K. Lee
*Director of the United States Patent and Trademark Office*

Col. 6, Line 67,
"second main channel by use of the on/off-valves. Each of the" should read
--second main channel by use of the on/off valves. Each of the--;

Col. 7, Line 21,
"may comprises preferably another pump, which in the fol-" should read
--may comprise preferably another pump, which in the fol- --;

Col. 7, Line 50,
"channel for supplying diluting fluid, e.g. water, for diluting" should read
--channel for supplying diluting fluid, e.g., water, for diluting--;

Col. 8, Line 27,
"As also described herein after, in one or more embodi-" should read
--As also described hereinafter, in one or more embodi- --;

Col. 11, Line 30,
"may, e.g. be embodied as metallic needles. Accordingly, each" should read
--may, e.g., be embodied as metallic needles. Accordingly, each--;

Col. 13, Line 54,
"subset of (e.g. two) processing units 3 coupled to the optical" should read
--subset of (e.g., two) processing units 3 coupled to the optical--;

Col. 13, Line 56,
"method and a second subset of (e.g. three) processing units 3" should read
--method and a second subset of (e.g., three) processing units 3--;

Col. 14, Line 25,
"connecting one processing unit 3 and one distribution channel" should read
--connects one processing unit 3 and one distribution channel--;

Col. 14, Line 33,
"channels 17, each of which fluidically connecting one reagent" should read
--channels 17, each of which fluidically connects one reagent--;

Col. 15, Line 4,
"Each of the processing units 3 (e.g. five processing units 3" should read
--Each of the processing units 3 (e.g., five processing units 3--;

Col. 15, Line 7,
"channel channels 18. Each first reagent supply channel 18" should read
--channels 18. Each first reagent supply channel 18--;

CERTIFICATE OF CORRECTION (continued)
U.S. Pat. No. 8,778,696 B2

Col. 15, Line 12,
"(e.g. three reagent containers 8 are shown for the purpose of" should read
--(e.g., three reagent containers 8 are shown for the purpose of--;

Col. 16, Line 23,
"e.g., five plug positions (e.g. sockets), each of which being" should read
--e.g., five plug positions (e.g., sockets), each of which being--;

Col. 16, Line 26,
"tion channels 13 which are embodied as (e.g. female) plug-in" should read
--tion channels 13 which are embodied as (e.g., female) plug-in--;

Col. 16, Line 32,
"the processing units 3 is provided with plural (e.g. male)" should read
--the processing units 3 is provided with plural (e.g., male)--;

Col. 16, Line 33,
"connectors 25 which can be connected (e.g. plugged-in) to the" should read
--connectors 25 which can be connected (e.g., plugged in) to the--;

Col. 17, Line 2,
"compact arrangement of the processing units 3, which, e.g." should read
--compact arrangement of the processing units 3, which, e.g.,--;

Col. 17, Line 39,
"channels 13 which are embodied as (e.g. female) plug-in" should read
--channels 13 which are embodied as (e.g., female) plug-in--;

Col. 18, Line 45,
"processing unit 3 contains gaseous system fluid, e.g. air, or" should read
--processing unit 3 contains gaseous system fluid, e.g., air, or--;

Col. 19, Line 43,
"In the processing unit 3, a number of, e.g. forty, reaction" should read
--In the processing unit 3, a number of, e.g., forty, reaction--;

Col. 21, Line 19,
"ied as two-way valve. The main wash unit 143 can be used for" should be
--ied as a two-way valve. The main wash unit 143 can be used for--;

Col. 21, Line 28,
"two-way valve. The auxiliary wash unit 145 can be used for" should be
--a two-way valve. The auxiliary wash unit 145 can be used for--;

Col. 21, Line 61,
"programmable logic controller running a computer-readable" should read
--a programmable logic controller running a computer-readable--;

Col. 22, Line 50,
"of the first reagent channels 118 (e.g. the marked outermost" should read
--of the first reagent channels 118 (e.g., the marked outermost--;

Col. 23, Line 28,
"both are sucked into one of the reaction chambers 120 (e.g." should read
--both are sucked into one of the reaction chambers 120 (e.g.,--;

Col. 23, Line 55,
"128 of one of the second reagent channels 127 (e.g. the" should read
--128 of one of the second reagent channels 127 (e.g., the--;

Col. 26, Line 8,
"freeze/thaw-valve 216 so as to enable or block sample flow" should read
--freeze/thaw valve 216 so as to enable or block sample flow--;

Col. 26, Line 10,
"ber 217. The first freeze/thaw-valve 216 of the sample chan-" should read
--ber 217. The first freeze/thaw valve 216 of the sample chan- --;

Col. 26, Line 25,
"second freeze/thaw-valve 219 so that reagent flow from the" should read
--second freeze/thaw valve 219 so that reagent flow from the--;

Col. 26, Line 27,
"217 can be enabled or blocked. The second freeze/thaw-" should read
--217 can be enabled or blocked. The second freeze/thaw--;

Col. 26, Line 41,
"a third freeze/thaw-valve 223 so as to enable or block fluid" should read
--a third freeze/thaw valve 223 so as to enable or block fluid--;

Col. 26, Line 54,
"freeze/thaw-valve 225 which partitions the first main channel" should read
--freeze/thaw valve 225 which partitions the first main channel--;

Col. 27, Line 25,
"freeze/thaw-valve 219 so that reagent flow from the second" should read
--freeze/thaw valve 219 so that reagent flow from the second--;

CERTIFICATE OF CORRECTION (continued)
U.S. Pat. No. 8,778,696 B2

Col. 27, Line 27,
"234 can be enabled or blocked. The second freeze/thaw-" should read
--234 can be enabled or blocked. The second freeze/thaw--;

Col. 28, Line 8,
"sample intake 250. The sample intake 150 is equipped with a" should read
--sample intake 250. The sample intake 250 is equipped with a--;

Col. 28, Line 65,
"a comparably large number (e.g. hundreds) of reagent" should read
--a comparably large number (e.g., hundreds) of reagent--;

Col. 29, Line 21,
"few moving part, thus avoiding frequent maintenance" should read
--few moving parts, thus avoiding frequent maintenance--;

In the Claims

Col. 30, Line 7, Claim 1,
"valve of said first main channel with said on/off-valve of" should read
--valve of said first main channel with said on/off valve of--; and Col. 30, Line 67, Claim 7,
"and second segments, each of which including:" should read
--and second segments, each of which includes:--.